(12) United States Patent
Makino et al.

(10) Patent No.: US 8,698,887 B2
(45) Date of Patent: Apr. 15, 2014

(54) IMAGE PICKUP APPARATUS, ENDOSCOPE AND MANUFACTURING METHOD FOR IMAGE PICKUP APPARATUS

(75) Inventors: Yukiharu Makino, Nagano (JP); Takashi Nakayama, Ina (JP); Fukashi Yoshizawa, Ina (JP); Takatoshi Igarashi, Nagano (JP)

(73) Assignee: Olympus Corporation, Tokyo (JP)

( * ) Notice: Subject to any disclaimer, the term of this patent is extended or adjusted under 35 U.S.C. 154(b) by 354 days.

(21) Appl. No.: 13/046,133

(22) Filed: Mar. 11, 2011

(65) Prior Publication Data

US 2011/0249106 A1 Oct. 13, 2011

(30) Foreign Application Priority Data

Apr. 7, 2010 (JP) .................................. 2010-088746
Sep. 17, 2010 (JP) .................................. 2010-209774

(51) Int. Cl.
*A61B 1/04* (2006.01)

(52) U.S. Cl.
USPC .......................................................... 348/76

(58) Field of Classification Search
USPC .......................................................... 348/76
See application file for complete search history.

(56) References Cited

U.S. PATENT DOCUMENTS

| | | | | |
|---|---|---|---|---|
| 5,021,888 A | * | 6/1991 | Kondou et al. | 348/76 |
| 5,754,313 A | * | 5/1998 | Pelchy et al. | 358/473 |
| 7,296,722 B2 | * | 11/2007 | Ivanko | 227/175.1 |
| 8,189,062 B2 | * | 5/2012 | Irion et al. | 348/222.1 |
| 2008/0111907 A1 | * | 5/2008 | Ito et al. | 348/311 |
| 2009/0021618 A1 | * | 1/2009 | Schwarz et al. | 348/294 |
| 2010/0073470 A1 | * | 3/2010 | Takasaki | 348/76 |
| 2011/0034769 A1 | * | 2/2011 | Adair et al. | 600/110 |

FOREIGN PATENT DOCUMENTS

| | | |
|---|---|---|
| JP | 04-072689 A | 3/1992 |
| JP | 04-218136 A | 8/1992 |
| JP | 2000-199863 | 7/2000 |
| JP | 2001-013662 | 1/2001 |
| JP | 2009-176815 | 8/2009 |

OTHER PUBLICATIONS

Japanese Office Action dated Dec. 3, 2013 in counterpart Japanese Patent Application No. 2010-088746.

* cited by examiner

*Primary Examiner* — Dave Czekaj
*Assistant Examiner* — Tyler W Sullivan
(74) *Attorney, Agent, or Firm* — Scully, Scott, Murphy & Presser, P.C.

(57) ABSTRACT

An image pickup apparatus having an image pickup device chip, a wiring board placed within a projection plane of the image pickup device chip and a reinforcement member fixed in abutment with at least a part of the wiring board. An endoscope having the image pickup apparatus. A method for manufacturing the image pickup apparatus.

16 Claims, 15 Drawing Sheets

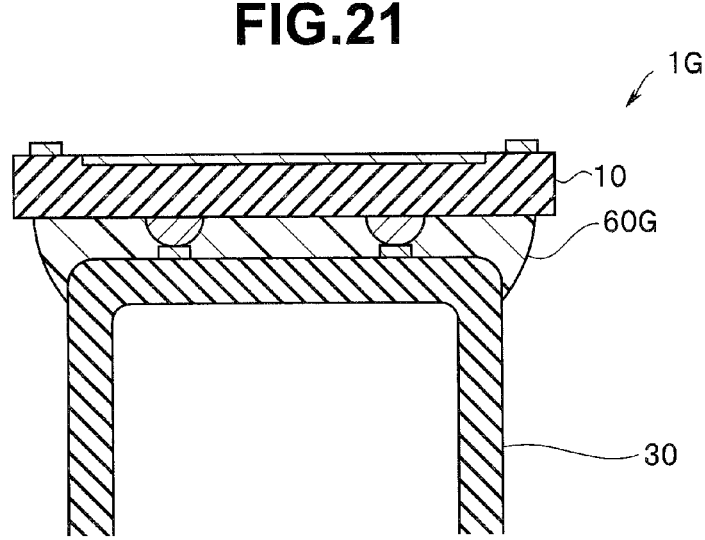
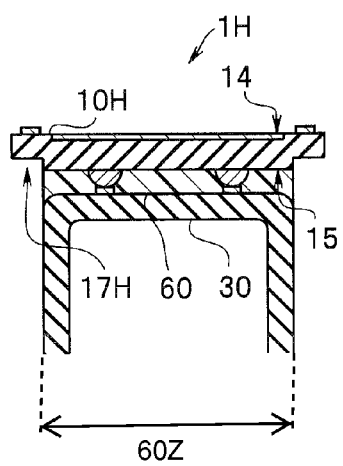 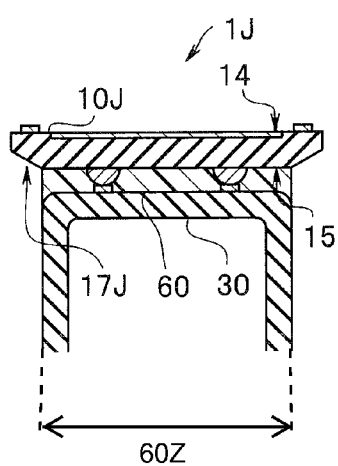 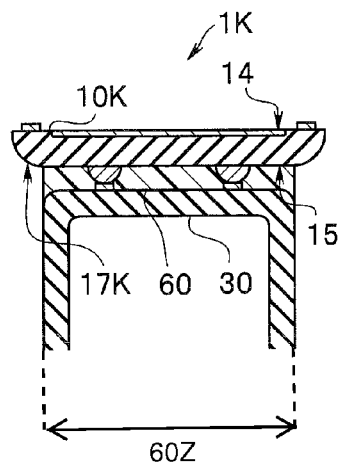

FIG.23
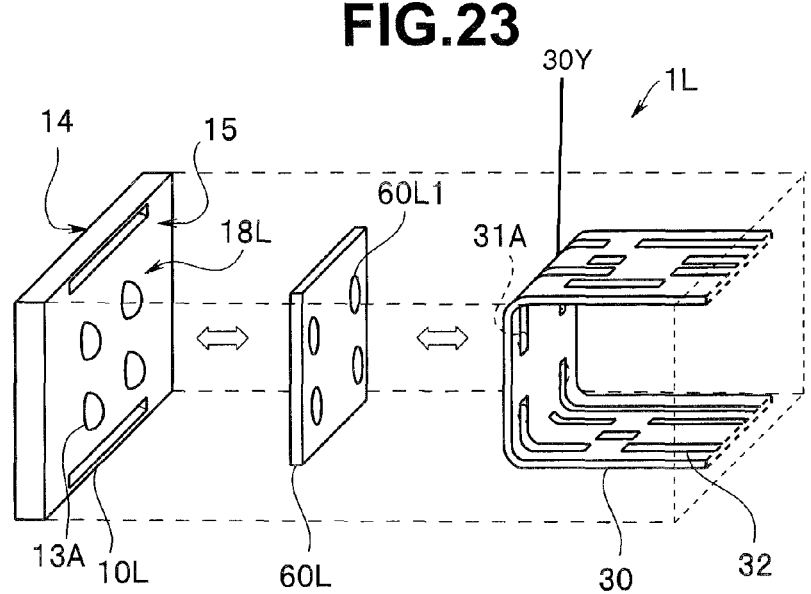
FIG.24A FIG.24B FIG.24C
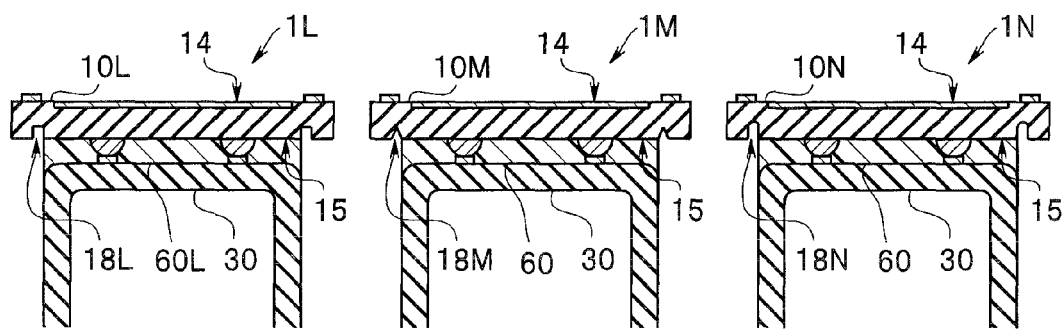

IMAGE PICKUP APPARATUS, ENDOSCOPE AND MANUFACTURING METHOD FOR IMAGE PICKUP APPARATUS

CROSS REFERENCE TO RELATED APPLICATION

This application claims the benefit of Japanese Application No. 2010-088746 filed in Japan on Apr. 7, 2010 and Japanese Application No. 2010-209774 filed in Japan on Sep. 17, 2010, the contents of which are incorporated herein by this reference.

BACKGROUND OF THE INVENTION

1. Field of the Invention

The present invention relates to an image pickup apparatus equipped with a solid-state image pickup device chip, an endoscope equipped with the image pickup apparatus, and a manufacturing method for the image pickup apparatus, and more particularly, to an image pickup apparatus connected with an external connection terminal on a rear face of a solid-state image pickup device chip and equipped with a wiring board having a flexing portion, an endoscope equipped with the image pickup apparatus, and a manufacturing method for the image pickup apparatus.

2. Description of the Related Art

An image pickup apparatus equipped with a solid-state image pickup device chip is used, for example, by being disposed in a distal end portion of an endoscope. Diameter and size reductions are important issues for the distal end portion of the endoscope to alleviate the pain of a patient.

As shown in FIG. 1, Japanese Patent Application Laid-Open Publication No. 2000-199863 discloses an image pickup apparatus 101 which includes an image pickup device chip 120, a pattern film 130, a wiring board 140, and a signal cable 150. The wiring board 140, electronic components 146 mounted on the wiring board 140, and a terminal portion of the signal cable 150 fit within a projection plane of the image pickup device chip 120.

As shown in FIG. 2, the wiring board 140 is a T-shaped multilayer ceramic board made up of a vertically-oriented substrate 140A and a horizontally-oriented substrate 140B orthogonal to the substrate 140A. A bonding pad 124 provided in an outer peripheral portion of an image pickup device 123 and a bonding pad (not shown) provided on the vertically-oriented substrate 140A coupled to the back of the image pickup device chip 120 are connected by the pattern film 130 on which a wiring pattern is formed. The electronic components 146 are mounted on the horizontally-oriented substrate 140B and the signal cable 150 is connected to a terminal portion 143 formed in an end portion of the horizontally-oriented substrate 140B.

However, in the image pickup apparatus 101, the pattern film 130 is placed on a side face of the image pickup device chip 120, increasing an external dimension of the image pickup apparatus by an amount equal to the thickness (dozens to hundreds of microns) of the pattern film 130.

In Japanese Patent Application Laid-Open Publication No. 2009-176815, the present applicant discloses a structural body on which a flexing portion is formed at a predetermined angle by abutting electronic components mounted on a wiring substrate against each other.

Also, Japanese Patent Application Laid-Open Publication No. 2001-013662 discloses a flip-chip mounting method for attaching a semiconductor device having input and output electrode terminals provided with conductive posts and covered with a partially cured resin to a circuit board under heat and pressure.

SUMMARY OF THE INVENTION

According to an embodiment of the present invention, there is provided an image pickup apparatus, comprising: an image pickup device chip having an image pickup device on a front face and an external connection terminal on a rear face, where the external connection terminal is connected to the image pickup device through a via interconnect; a wiring board placed within a projection plane of the image pickup device chip and made up of an intermediate portion whose first main face is connected with the external connection terminal, a first flexing portion and a second flexing portion extended from opposite ends of the intermediate portion and bent toward the intermediate portion at a predetermined angle, and a first extension portion and a second extension portion extended from the first flexing portion or the second flexing portion; and a signal cable connected to at least one of the first extension portion and the second extension portion.

According to another embodiment, there is provided an endoscope, comprising: an image pickup device chip having an image pickup device on a front face and an external connection terminal on a rear face, where the external connection terminal is connected to the image pickup device through a via interconnect; a wiring board placed within a projection plane of the image pickup device chip and made up of an intermediate portion whose first main face is connected with the external connection terminal, a first flexing portion and a second flexing portion extended from opposite ends of the intermediate portion and bent toward the intermediate portion at a predetermined angle, and a first extension portion and a second extension portion extended from the first flexing portion or the second flexing portion; and a signal cable connected to at least one of the first extension portion and the second extension portion.

According to another embodiment, there is provided a manufacturing method for an image pickup apparatus, comprising: an image pickup device chip production step of producing an image pickup device chip having an image pickup device on a front face and an external connection terminal on a rear face, where the external connection terminal is connected to the image pickup device through a via interconnect; an external connection terminal connection step of connecting a first main face in an intermediate portion of a wiring board with the external connection terminal; a reinforcement member bonding step of bonding a reinforcement member to a second main face in the intermediate portion of the wiring board; a wiring board fixing step of bending a first flexing portion and a second flexing portion extended from opposite ends of the intermediate portion of the wiring board toward the intermediate portion at a predetermined angle, fixing at least part of a second main face in a first extension portion and a second extension portion extended from the first flexing portion or the second flexing portion in abutment with the reinforcement member, and thereby placing the wiring board within a projection plane of the image pickup device chip; and a cable connection step of connecting a signal cable to at least one of the first extension portion and the second extension portion.

BRIEF DESCRIPTION OF THE DRAWINGS

FIG. 21 is a sectional view for illustrating an image pickup apparatus according to a second variation of the sixth embodiment;

FIGS. 22A to 22C are sectional views for illustrating an image pickup apparatus according to a seventh embodiment;

FIG. 23 is an exploded view for illustrating an image pickup apparatus according to an eighth embodiment;

FIGS. 24A to 24C are sectional views for illustrating the image pickup apparatus according to the eighth embodiment;

DETAILED DESCRIPTION OF THE PREFERRED EMBODIMENTS

<First Embodiment>

Figure 1:
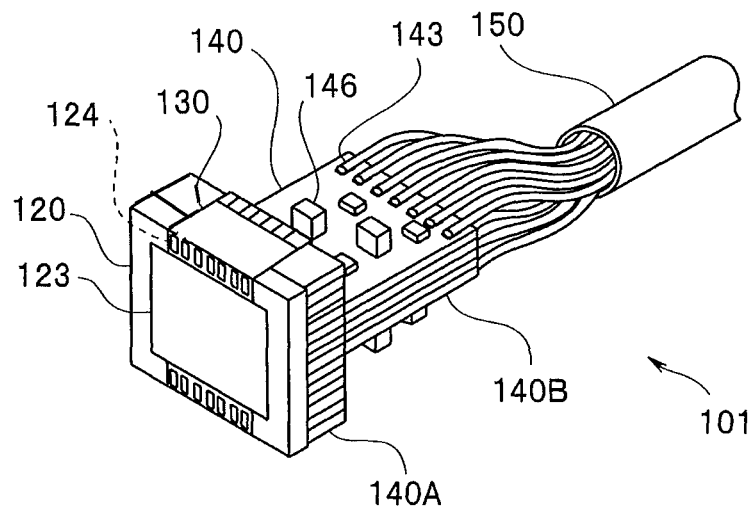
FIG. 1 is a perspective view for illustrating a structure of a known image pickup apparatus.
Figure 2:
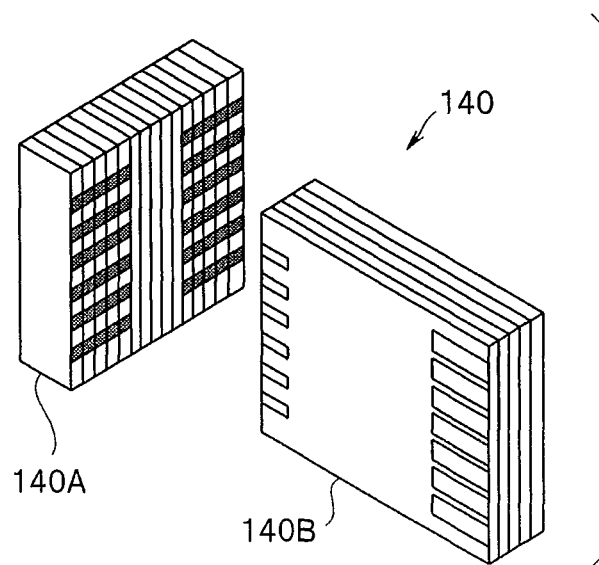
FIG. 2 is an exploded view for illustrating a structure of a wiring board of a known image pickup apparatus.
Figure 3:
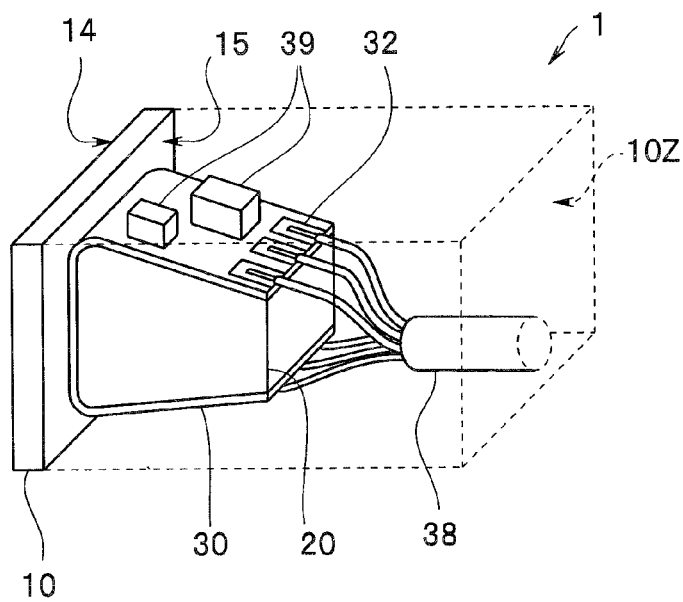
FIG. 3 is a perspective view for illustrating a structure of an image pickup apparatus according to a first embodiment.
Figure 4:
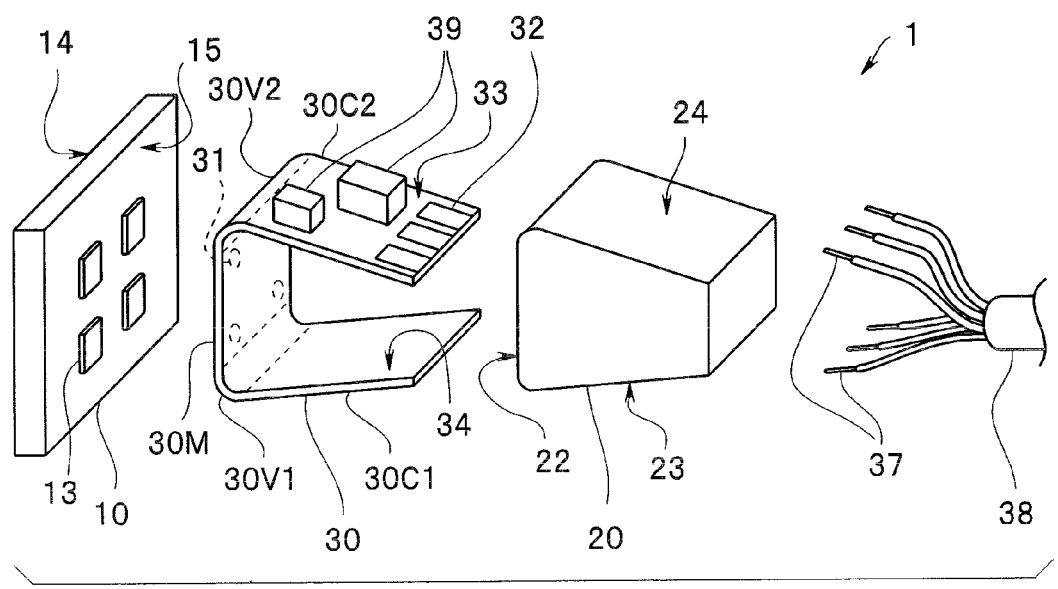
FIG. 4 is an exploded view for illustrating the structure of the image pickup apparatus according to the first embodiment.
Figure 5:
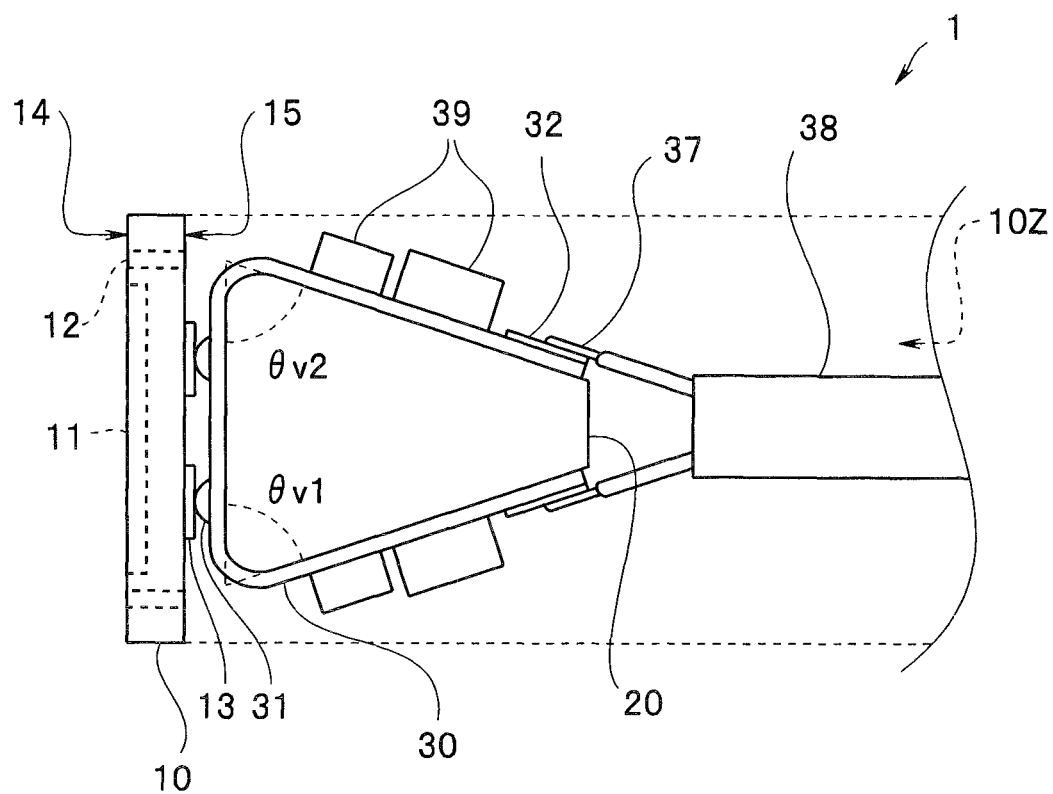
FIG. 5 is an explanatory diagram showing a state viewed from a lateral direction to illustrate the structure of the image pickup apparatus according to the first embodiment.

As shown in FIGS. 3, 4, and 5, an image pickup apparatus 1 according to the present embodiment is a solid-state image pickup apparatus which includes an image pickup device chip 10, a block 20 which is a reinforcement member, a wiring board 30, and a signal cable (hereinafter also referred to as a "cable") 38.

An image pickup device 11 (see FIG. 5) such as a CMOS device is formed on a front face 14 which is a first main face of the image pickup device chip 10, and external connection terminals 13 of the image pickup device 11 are formed on a rear face 15 which is a second main face through via interconnects 12 using TSVs (Through-Silicon Vias) or the like.

The wiring board 30 provided with a first main face 33 and a second main face 34 is a flexible wiring board using a flexible resin such as polyimide as base material. On the first main face 33, the wiring board 30 has a wiring layer (not shown) made of copper or the like and connected with the external connection terminals 13 of the image pickup device chip 10 via connection portions 31 such as gold bumps, the connection portions (not shown) connected with the wiring layer and used to surface-mount electronic components 39, and multiple terminal portions 32 connected with the wiring layer and used to connect to a cable 38 containing multiple conductive wires 37. That is, the wiring layer connects the image pickup device chip 10 with the cable 38 and makes up an electronic circuit.

Incidentally, although the wiring board 30 is expressed as being divided into an intermediate portion 30M, a first flexing portion 30V1, a second flexing portion 30V2, a first extension portion 30C1, and a second extension portion 30C2 for the sake of convenience, actually the wiring board 30 according to the present embodiment is a single flexible wiring board and boundaries among the divided portions described above are not defined clearly. The wiring board needs only that at least the first flexing portion 30V1 and the second flexing portion 30V2 have flexibility, and may be a rigid-flexible wiring board in which intermediate portion 30M, the first extension portion 30C1, and the second extension portion 30C2 are made of rigid material. In the case of a rigid-flexible wiring board, the boundaries among the divided portions are clear. The cable 38 transmits signals and the like between the image pickup device chip 10 and other units (not shown) including a control unit and a signal processing unit.

The image pickup apparatus 1 includes the block 20 which is a reinforcement member adapted to bend and hold the first flexing portion 30V1 and the second flexing portion 30V2 of the wiring board 30 toward the intermediate portion 30M at a predetermined angle. The block 20 includes a bonding surface 22 bonded to the second main face 34 of the wiring board 30, and two inclined surfaces 23 and 24 inclined inward at a predetermined angle on both sides of the bonding surface 22.

The wiring board 30 is bent along the block 20, and flexing angles θv1 and θv2 of the first flexing portion 30V1 and second flexing portion 30V2 are determined by inclined angles θv1 and θv2 of the inclined surfaces 23 and 24 of the block 20. Bent portions of the first flexing portion 30V1 and the second flexing portion 30V2 have a curved shape, and an angle between the intermediate portion 30M and the first extension portion 30C1 as well as between the intermediate portion 30M and the second extension portion 30C2 are designated as a bending angle (flexing angle) θv. When the bending angle θv is less than 90 degrees, the first extension portion 30C1 and the second extension portion 30C2 are inclined toward the intermediate portion 30M. Preferably the bending angle θv is 90 to 50 degrees, and more preferably 75 to 55 degrees such as 65 degrees. Incidentally, as described later, depending on mounting conditions of the electronic components 39 on the wiring board 30, most preferably the bending angle θv may be 90 degrees.

If the bending angle θv is within the range described above, the wiring board 30, the multiple electronic components 39 mounted on the wiring board 30, and a bonding portion of the cable 38 can be placed within a projection plane 10Z of the image pickup device chip 10. Here, the projection plane 10Z is a vertical projection plane parallel to the front face 14 and the rear face 15. The phrase "within the projection plane 10Z" means the inside of multiple projection planes 10Z, in other words, the inside of a space formed by the multiple projection planes 10Z.

Incidentally, the flexing angle θv1 of the first flexing portion 30V1 and the flexing angle θv2 of the second flexing portion 30V2 may be either equal flexing angles θv or different flexing angles as long as the range described above is satisfied. Also, since the cable 38 has flexibility, for diameter reduction of the image pickup apparatus 1, there is no need to place the entire length of the cable 38 within the projection plane 10Z, and it is sufficient if at least the bonding portion with respect to the wiring board 30 is placed within the projection plane 10Z.

The block 20 functions as a fixing member adapted to place the wiring board 30 within a predetermined space, i.e., within the projection plane 10Z of the image pickup device chip 10. Also, the block 20 holds the wiring board 30 stably and functions to facilitate the bonding operation of the cable 38 to the wiring board 30.

Furthermore, the block 20 also functions as a reinforcement member adapted to increase mechanical strength by holding the image pickup device chip 10 and the wiring board 30 integrally. That is, the image pickup device chip 10, which is formed, for example, on a silicon substrate, might be deformed or broken by external forces. However, the image pickup device chip 10 is bonded to the block 20 via the wiring board 30, resulting in increased strength. Similarly, the wiring board 30 increases in strength by being bonded to the block 20 although substantially loses flexibility.

As described above, in the image pickup apparatus 1 according to the present embodiment, the wiring board 30, which is fixed in abutment with the block 20, constantly remains flexed at a predetermined angle even if a special jig or the like is not used. That is, since the wiring board 30 and the like can be placed in a predetermined small space, the image pickup apparatus 1 readily lends itself to reductions in external dimensions. Thus, the image pickup apparatus 1 can be disposed stably in the predetermined small space.

Next, a manufacturing method for the image pickup apparatus 1 will be described with reference to FIGS. 6A to 6D.

The image pickup device chip 10, the block 20, the wiring board 30, and the cable 38 are produced separately and subsequently integrated in an assembly step.

The image pickup device chip 10 is produced by dicing an image pickup device wafer made up of a large number of image pickup devices 11 and via interconnects 12 formed, for example, on a silicon substrate, using a known semiconductor process. That is, an image pickup device chip production step produces the image pickup device chips 10 having the image pickup devices 11 on the front face 14 and the external connection terminals 13 on the rear face, where the external connection terminals 13 are connected to the image pickup devices 11 through the via interconnects 12.

When made of a resin such as polycarbonate, the block 20 is produced by die casting or the like. The wiring board 30 is produced by applying etching and plating or the like to a copper foil and polyimide or other base material affixed to each other.

Figure 6A:
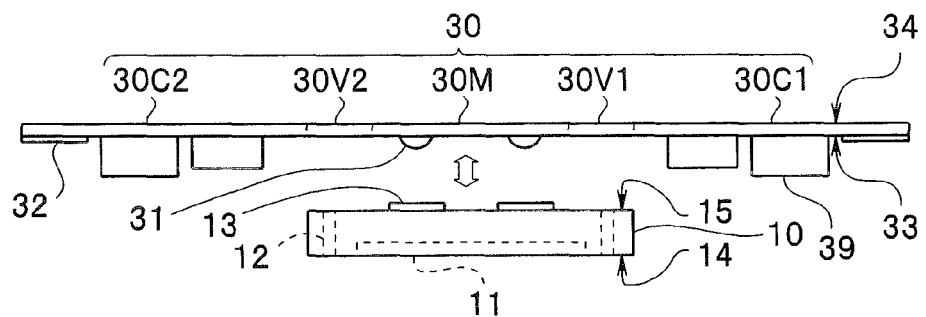
FIGS. 6A to 6D are explanatory diagrams showing a state viewed from a lateral direction to illustrate a manufacturing method for the image pickup apparatus according to the first embodiment.

Then, as shown in FIG. 6A, the electronic components 39 are mounted on the first main face 33 in the first extension portion 30C1 and second extension portion 30C2 of the wiring board 30. The electronic components 39 are components selected, as required, from among chip capacitors, chip resistors, signal processing ICs, driver ICs, power supply ICs, diodes, coils, reed switches, and the like. Of course, electronic components 39 do not need to be mounted if there is no need for them.

Next, in a connection step (external connection terminal connection step), the wiring layer in the intermediate portion 30M of the wiring board 30 is connected to the external connection terminals 13 on the rear face 15 of the image pickup device chip 10 via the connection portions 31. As described later, a gap between the wiring board 30 and the image pickup device chip 10 may be sealed/bonded by resin. Also, solder bumps (solder balls), an ACP (anisotropic conductive resin paste), an ACF (anisotropic conductive film), or the like may be used for the connecting.

Figure 6B:
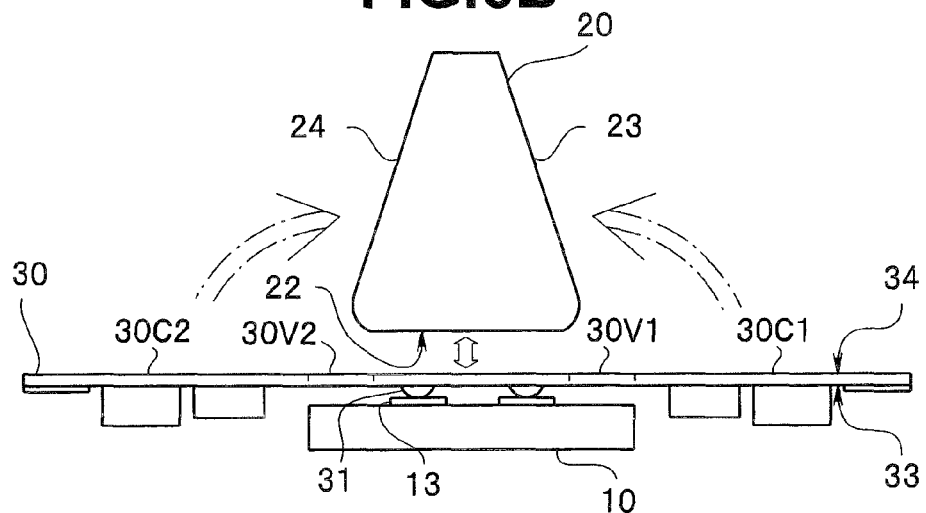

Next, as shown in FIG. 6B, in a reinforcement member bonding step, the bonding surface 22 of the block 20 is bonded to the second main face 34 in the intermediate portion 30M of the wiring board 30 via a bonding layer 60 described later (see FIG. 28 and the like). Besides, available materials of the block 20 made of resin includes PET (polyethylene terephthalate), fluororesin, acrylic resin, polyacetal, polypropylene, polyethylene, and silicon. The area of the bonding surface 22 of the block 20 has only to be smaller than the area of the rear face 15 of the image pickup device chip 10.

Figure 6C:
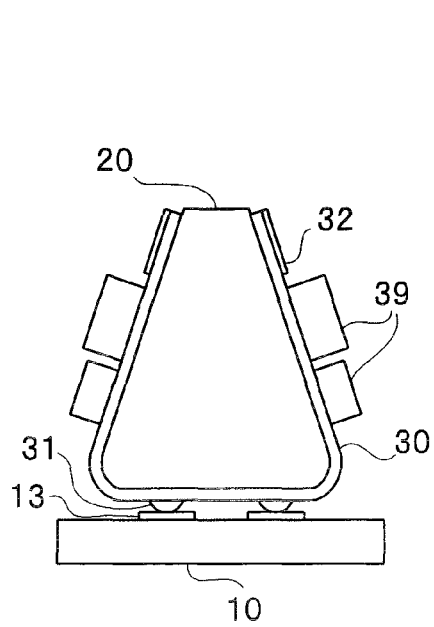

Then, as shown in FIG. 6C, in a wiring board fixing step (bending step), after an adhesive (not shown) is applied to at least one of the second main face 34 in the first extension portion 30C1 and second extension portion 30C2 of the wiring board 30 and the inclined surfaces 23 and 24 of the block 20, the first flexing portion 30V1 and the second flexing portion 30V2 of the wiring board 30 are bent such that the first extension portion 30C1 and the second extension portion 30C2 will abut the inclined surfaces 23 and 24 of the block 20. The same material as the bonding layer 60 used to bond the bonding surface 22 may be used to bond the inclined surfaces 23 and 24. As the adhesive is cured with the first extension portion 30C1 and the second extension portion 30C2 placed in abutment with the inclined surfaces 23 and 24 of the block 20, the first extension portion 30C1 and the second extension portion 30C2 are bonded to the inclined surfaces 23 and 24. Incidentally, a space may be left to separate the block 20 from the first flexing portion 30V1 and the second flexing portion 30V2 or may be filled with an adhesive or the like.

In the image pickup apparatus 1, since the flexing angles of the first flexing portion 30V1 and the second flexing portion 30V2 are determined by the angles of the inclined surfaces 23 and 24 of the block 20, the first flexing portion 30V1 and the second flexing portion 30V2 can be flexed at a predetermined angle easily and accurately. Also, the wiring board 30, which abuts the block 20 by surface contact over a large contact area, can be flexed easily without being stressed excessively, and consequently without danger of breakage.

From the viewpoint of preventing wiring layer disconnection, preferably flexing shape of the first flexing portion 30V1 and second flexing portion 30V2 is a curved shape which is less vulnerable to stress, but the shape does not make much difference as long as the first flexing portion 30V1 and second flexing portion 30V2 including the electronic components 39 and the cable 38 fit within the projection plane 10Z of the image pickup device chip 10.

Figure 6D:
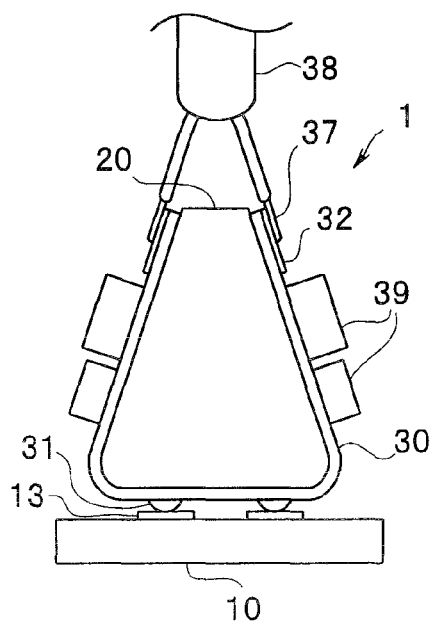

Finally, as shown in FIG. 6D, in a cable connection step, conductive wires 37 of the cable 38 are electrically connected with the terminal portions 32 of the first extension portion 30C1 and second extension portion 30C2 of the wiring board 30, for example, by solder joints. In the image pickup apparatus 1, since the wiring board 30 is held stably by the block 20, the cable 38 can be connected easily to the terminal portions 32 by soldering. Besides, there is no need for a special jig used to temporarily fix the wiring board 30 during a solder-based connecting operation. Incidentally, the cable 38 may be connected to at least one of the first extension portion 30C1 and the second extension portion 30C2.

Since the wiring board 30 connected to the rear face 15 of the image pickup device chip 10, the electronic components 39 mounted on the wiring board 30, the connection portions of the cable 38 connected to the wiring board 30 are placed within the projection plane 10Z of the image pickup device chip 10, the image pickup apparatus 1 can be disposed in a small space. Also, the manufacturing method for the image pickup apparatus 1 enables efficient manufacturing of the image pickup apparatus 1 which can be disposed in a small space.

<Second Embodiment>

Next, an image pickup apparatus 1A according to a second embodiment will be described. The image pickup apparatus 1A according to the present embodiment is similar to the image pickup apparatus 1 according to the first embodiment, and the same components as those in the first embodiment are denoted by the same reference numerals as the corresponding components, and description thereof will be omitted.

Figure 7:
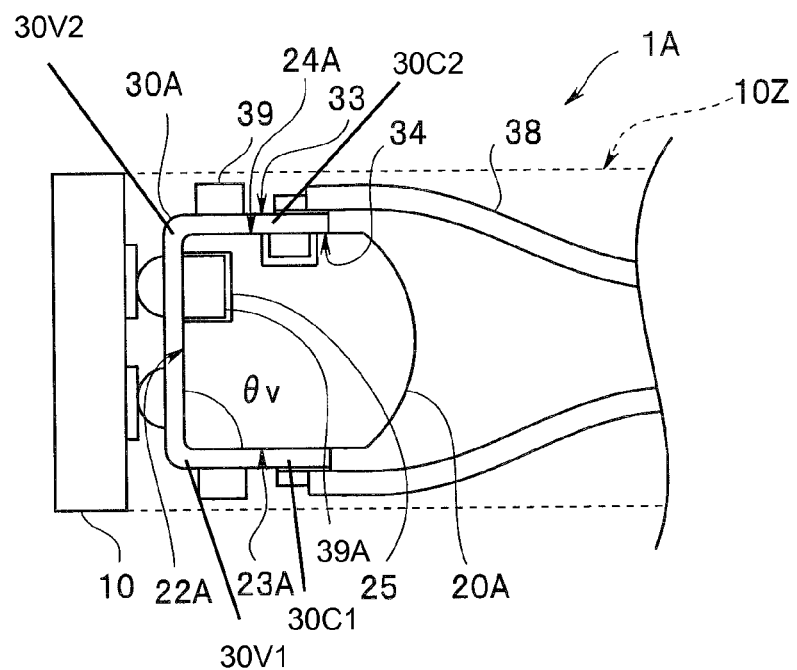
FIG. 7 is an explanatory diagram showing a state viewed from a lateral direction to illustrate a structure of an image pickup apparatus according to a second embodiment.

As shown in FIG. 7, a wiring board 30A of the image pickup apparatus 1A according to the present embodiment is a multilayer wiring board which has a wiring layer 35 (see FIG. 11) on at least both faces, and multiple electronic components 39 and 39A are mounted on the first main face 33 and the second main face 34, respectively. On the other hand, a block 20A which is a reinforcement member has a concave portion 25 inclined surfaces 23A and 24A, and a bonding surface 22A. The electronic components 39A mounted on the second main face 34 of the wiring board 30A are housed in the concave portion 25. In other words, the concave portion 25 is an opening for use to house the electronic components 39A. Incidentally, a gap between the concave portion 25 and the electronic components 39A may be either left as a space (air) or filled with an adhesive or the like.

Also, as shown in FIG. 7, in the image pickup apparatus 1A, the bending angle θv of the first flexing portion 30V1 and second flexing portion 30V2 of the wiring board 30A is approximately 90 degrees. However, since large electronic components 39A are located on the side of the block 20A, the wiring board 30A on which the electronic components 39 are mounted is placed within the projection plane 10Z of the image pickup device chip 10. That is, in the image pickup apparatus 1A, since the large electronic components 39A are mounted only on the second main face 34, there is no need to flex the first flexing portion 30V1 and the second flexing portion 30V2 greatly and a flexing angle θv of about 90 degrees is enough. Thus, there is no danger of wiring layer disconnection.

Also, since electronic components are mounted on both faces of the wiring board 30A, the image pickup apparatus 1A is provided with great flexibility in placement of the electronic components 39, making wiring board design easier. Also, since the electronic components can be mounted in a small area, the first extension portion 30C1 and the second extension portion 30C2 can be reduced in length. This allows the overall length of the image pickup apparatus to be reduced.

That is, in addition to the advantages of the image pickup apparatus 1 according to the first embodiment, the image pickup apparatus 1A according to the present embodiment provides greater reductions in diameter and size, thereby allowing placement in a smaller space.

<Third Embodiment>

Figure 8:
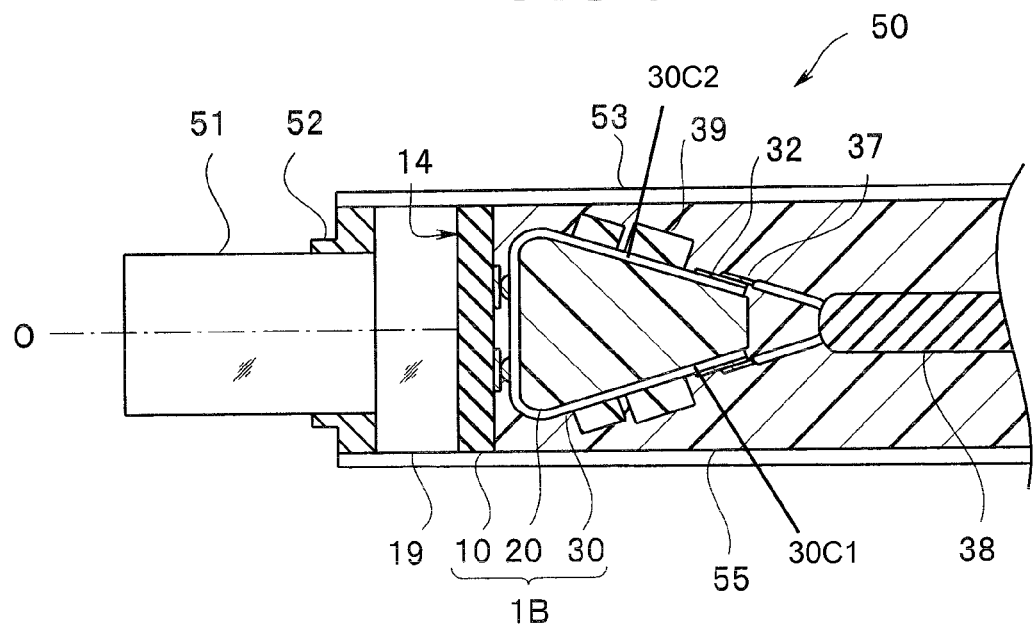
FIG. 8 is an explanatory diagram showing a state viewed from a lateral direction to illustrate a structure of an endoscope according to a third embodiment.

Next, an endoscope 50 with an image pickup apparatus 1B built into a distal end portion of an insertion portion will be described as a third embodiment with reference to FIG. 8. In FIG. 8, the image pickup apparatus 1B and an optical system 51 shown schematically are fixed with an optical axis O as a center by a frame portion 52. A back side of the image pickup apparatus 1B is covered by a shielding frame 53, and the inside of the shielding frame 53 is filled with an electrically nonconductive resin filler 55 with high thermal conductivity.

The image pickup apparatus 1B has a structure similar to the image pickup apparatus 1 described earlier and includes the image pickup device chip 10, the wiring board 30, and the block 20. Cover glass 19 is bonded to the front face 14 of the image pickup device chip 10. The electronic components 39 are mounted on the first extension portion 30C1 and second extension portion 30C2 of the wiring board 30, and the terminal portions 32 are connected with the cable 38.

The endoscope 50 with the above structure, i.e., with the image pickup apparatus 1B built into the distal end portion of the insertion portion, lends itself to diameter reduction.

<Fourth Embodiment>

Next, an image pickup apparatus 1C according to a fourth embodiment will be described. The image pickup apparatus 1C according to the present embodiment is similar to the image pickup apparatus 1A according to the second embodiment, and the same components as those in the second embodiment are denoted by the same reference numerals as the corresponding components, and description thereof will be omitted.

Figure 9:
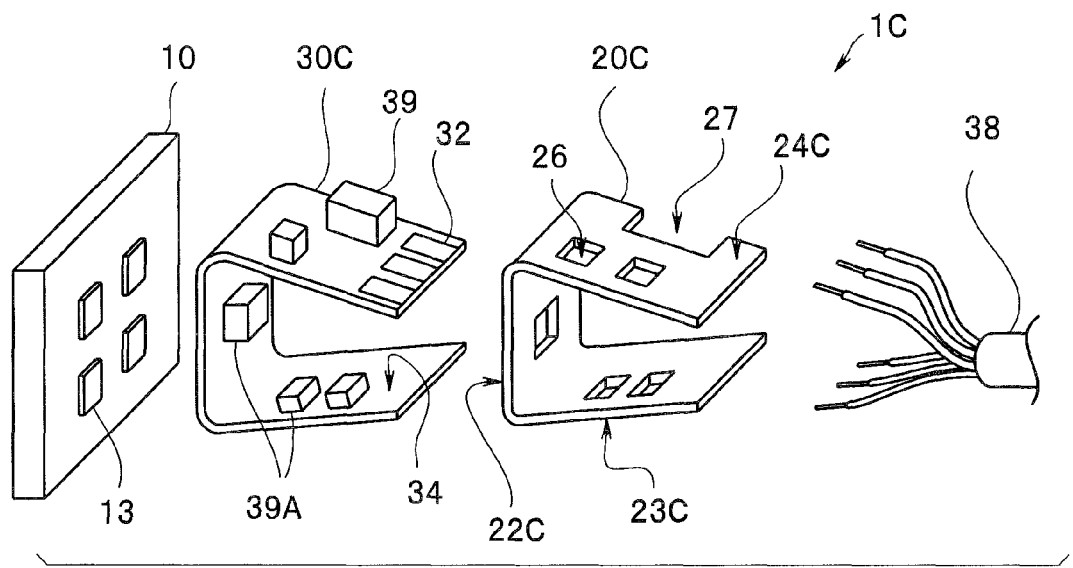
FIG. 9 is an exploded view for illustrating a structure of an image pickup apparatus according to a fourth embodiment.

As shown in FIG. 9, a reinforcement member of the image pickup apparatus 1C according to the present embodiment is a plate 20C. The plate 20C is produced by flexing opposite ends of a plate at a predetermined angle. As with the block 20A, the plate 20C includes a bonding surface 22C bonded to the second main face 34 of a wiring board 30C as well as inclined surfaces 23C and 24C inclined inward at a predetermined angle with respect to the bonding surface 22C. The bonding surface 22C and the inclined surfaces 23C and 24C have holes 26 and a cut portion 27. The holes 26 or the cut portion 27 are larger in size than the electronic components 39A mounted on the second main face 34 of the wiring board 30C. Consequently, the electronic components 39A mounted on the second main face 34 of the wiring board 30C are housed through the openings, i.e., the holes 26 or cut portion 27.

Available materials for the plate 20C include resin, ceramics, and metal.

As described above, the image pickup apparatus 1C according to the present embodiment has the advantages of the image pickup apparatus 1A according to the second embodiment and is lighter in weight than the image pickup apparatus 1A.

<Fifth Embodiment>

Next, an image pickup apparatus 1D according to a fifth embodiment will be described. The image pickup apparatus 1D according to the present embodiment is similar to the image pickup apparatus 1A according to the second embodiment, and the same components as those in the second embodiment are denoted by the same reference numerals as the corresponding components, and description thereof will be omitted.

Figure 10:
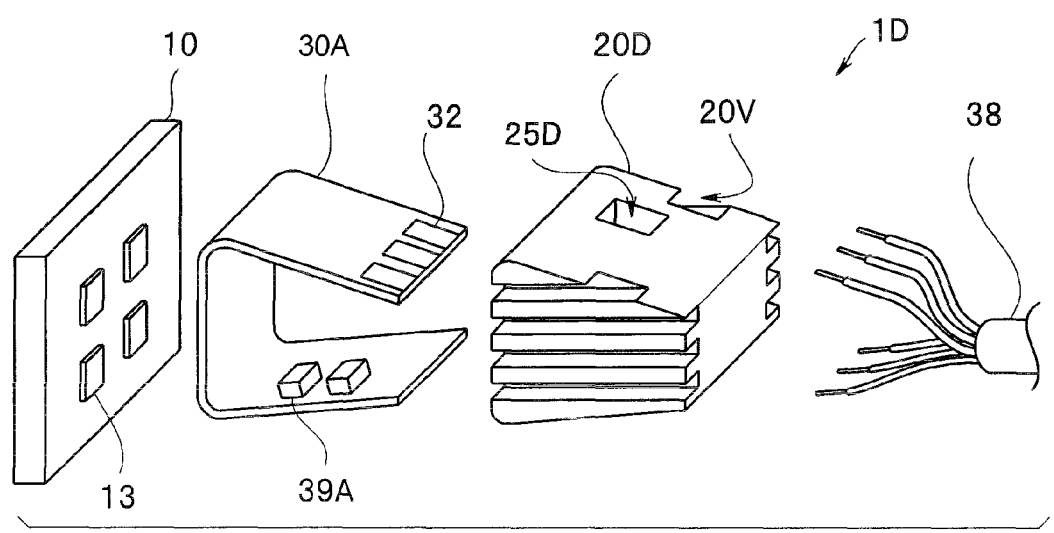
FIG. 10 is an exploded view for illustrating a structure of an image pickup apparatus according to a fifth embodiment.

As shown in FIG. 10, a reinforcement member of the image pickup apparatus 1D according to the present embodiment is a block 20D made of material with high thermal conductivity and serves as a heatsink provided with a heat dissipation function for dissipating heat generated by the image pickup device chip 10 and the like. Grooves 20V are formed in surfaces of the block 20D to provide an increased surface area and thereby enhance the heat dissipation function. Preferably the block 20D is made of a metal material with high thermal conductivity, such as aluminum and copper. Also, a concave portion 25D of the block 20D can house electronic components 39A.

The image pickup apparatus 1D, whose block 20D has the heat dissipation function, provides stable operation of the image pickup device chip 10 in addition to the advantages of the image pickup apparatus 1A according to the second embodiment.

<Sixth Embodiment>

Next, a sixth embodiment will be described. The sixth embodiment is similar to the first embodiment and the like, and the same components as those in the first embodiment and the like are denoted by the same reference numerals as the corresponding components while similar components are denoted by the same reference numerals with an alphabetical letter added to the end, and description thereof will be omitted.

Figure 11:
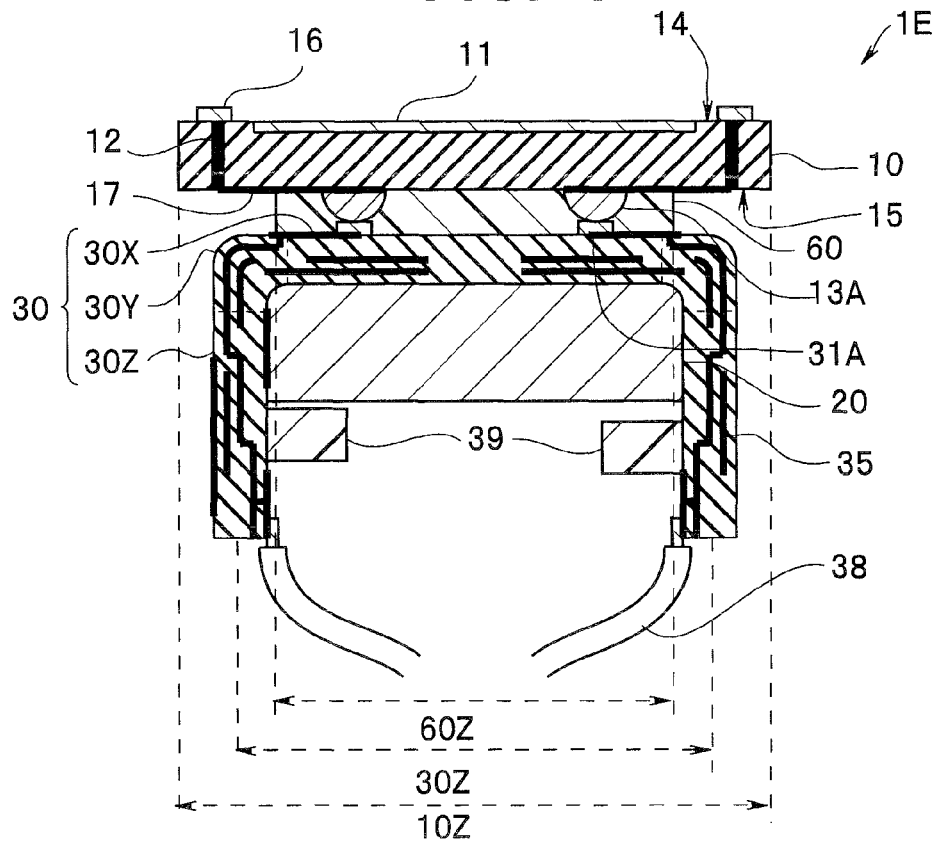
FIG. 11 is a sectional view for illustrating a structure of an image pickup apparatus according to a sixth embodiment.
Figure 12:
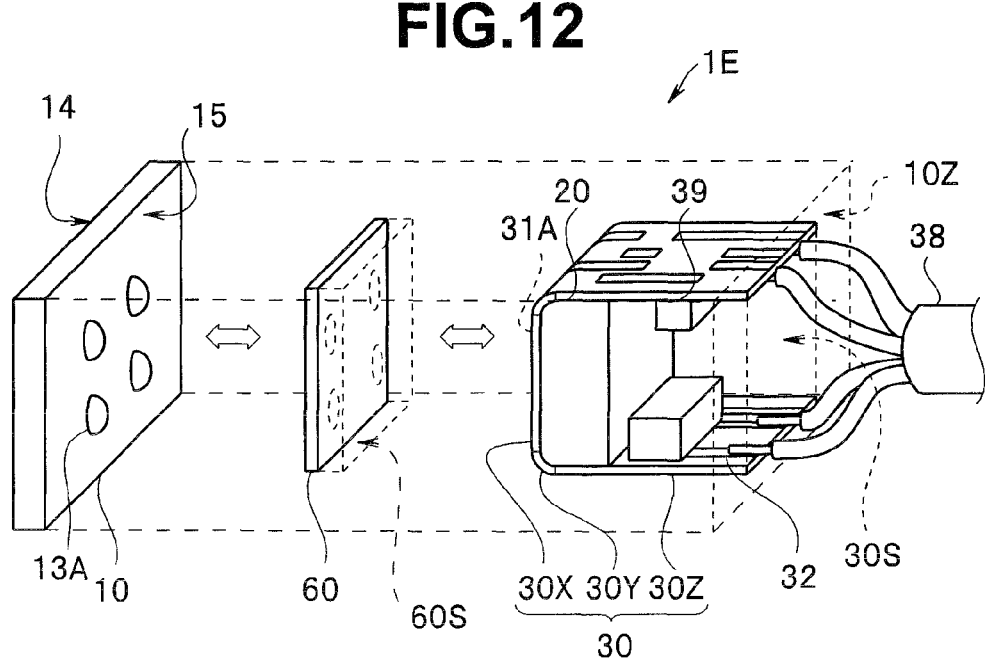
FIG. 12 is an exploded view for illustrating the structure of the image pickup apparatus according to the sixth embodiment.

As shown in FIGS. 11 and 12, the image pickup apparatus 1E according to the present embodiment includes the image pickup device chip 10, the bonding layer 60, and the wiring board 30. The image pickup device chip 10 is flip-chip-mounted on the wiring board 30 via the bonding layer 60. In other words, a gap between the wiring board 30 and the image pickup device chip 10 is sealed/bonded by the bonding layer 60.

As described earlier, connection terminals 16 on the front face 14 which is the first main face is connected with external connection terminals 13A on the rear face 15 which is the second main face through the via interconnects 12.

The via interconnects 12 are disposed in outer peripheral portions of the image pickup device 11. Preferably the external connection terminals 13A are disposed on inner sides of the via interconnects 12. That is, if the external connection terminals 13A are disposed close to the outer periphery of the image pickup device chip 10, it may be difficult to dispose the wiring board 30 within the projection plane 10Z of the image pickup device chip 10. Therefore, the image pickup device chip 10 uses a rear side interconnects 17 to dispose the external connection terminal 13A on the inner sides of formation regions of the via interconnects 12.

The external connection terminals 13A connected with the via interconnects 12 are, for example, gold bumps, copper bumps, solder bumps, or the like.

The wiring board 30 is a flexible multilayer wiring board using a flexible resin such as polyimide as base material. The wiring board 30 includes the wiring layer 35 made of copper or the like and connected with the external connection terminals 13A of the image pickup device chip 10 via connection portions (connection pads) 31A. The connection portions 31A may be part of the outermost layer of the wiring layer 35.

In the following embodiments, the wiring board 30 is expressed as being made up of a bonding portion 30X, bent portions 30Y, and extension portions 30Z, which correspond, respectively, to the intermediate portion 30M, first flexing portion 30V1 and second flexing portion 30V2, and first extension portion 30C1 and second extension portion 30C2 of the wiring board 30 according to the first embodiment described earlier. That is, the wiring board 30 is placed within the projection plane 10Z of the image pickup device chip 10 by being bent at the bent portions 30Y.

As described earlier, the block 20 functions as a reinforcement member and the like when the wiring board 30 is bent at the bent portions 30Y.

The bonding layer 60 is made, for example, of an anisotropic conductive film (ACF). The bonding layer 60 electrically connects the connection terminals 16 and the connection portions 31A with each other and has the functions to seal and reinforce connected portions. Preferably thickness of the bonding layer 60 is larger than height of the external connection terminals 13A to prevent cavity formation in bonded space. For that, the image pickup device chip 10 and the wiring board 30 are bonded together under pressure applied via the bonding layer 60. Heating or UV light irradiation may be used during bonding under pressure to melt solder or cure resin.

Incidentally, a microlens may be formed on the image pickup device 11 of the image pickup device chip 10 or a cover glass may be bonded to the image pickup device 11 via an air gap.

The image pickup apparatus 1E is configured to satisfy the relationship: (projection plane 10Z of the image pickup device chip) (projection plane 30Z of the wiring board)≥ (projection plane 60Z of the bonding layer). In other words, the wiring board 30 is placed within the projection plane of the image pickup device chip 10 and the bonding layer 60 is placed within the projection plane of the wiring board 30.

The sectional area of the image pickup apparatus 1E corresponds to the area of the projection plane of the image pickup device chip 10, and thus the image pickup apparatus 1E can be disposed in a small space. The endoscope which has the image pickup apparatus 1E disposed in the distal end portion lends itself to diameter reduction of the distal end portion.

Next, a manufacturing method for the image pickup apparatus 1E will be described with reference to FIGS. 13 to 18.

<Image Pickup Device Wafer Production Step>

Figure 13:
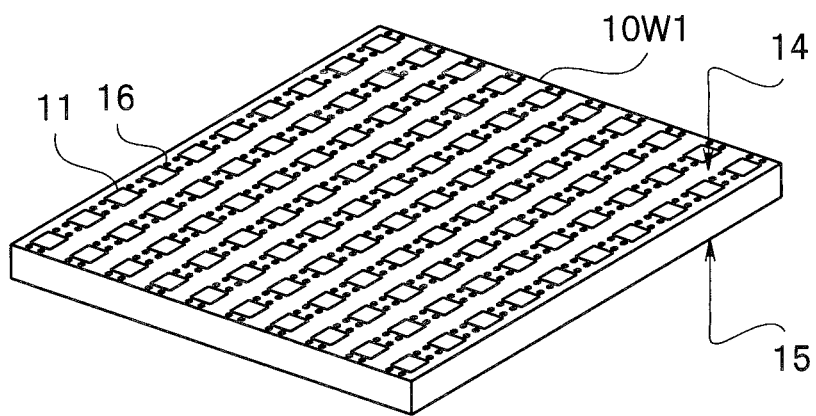
FIG. 13 is a perspective view from the side of a first main face for illustrating an image pickup device wafer production step of a manufacturing method for the image pickup apparatus according to the sixth embodiment.
Figure 14:
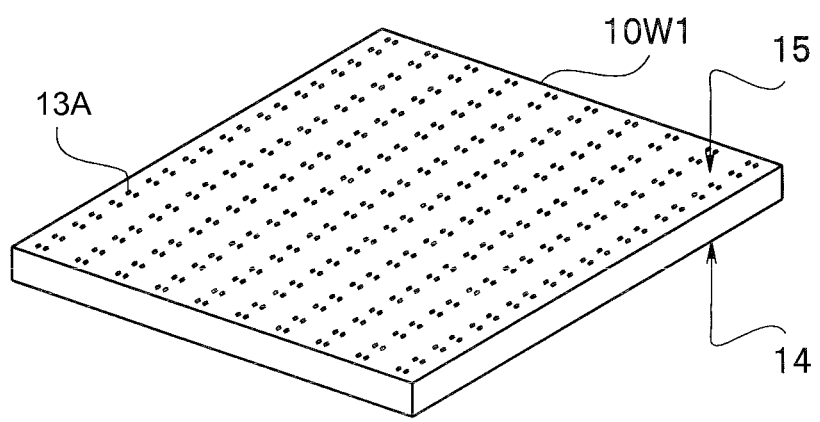
FIG. 14 is a perspective view from the side of a second main face for illustrating the image pickup device wafer production step of the manufacturing method for the image pickup apparatus according to the sixth embodiment.

As shown in FIGS. 13 and 14, this step produces an image pickup device wafer 10W1 which has a plurality of the image pickup devices 11 and a plurality of the connection terminals 16 on the front face 14 and has the external connection terminals 13A on the rear face 15, where the plurality of the connection terminals 16 are connected to the respective image pickup devices 11 and the external connection terminals 13A are connected to the respective connection terminals 16.

The image pickup device wafer 10W1 shown in FIGS. 13 and 14 is a single wafer containing 100 image pickup devices 11 arranged in a 10×10 matrix, 400 connection terminals 16, and 400 external connection terminals 13A. That is, one image pickup device 11 has four connection terminals 16, which are connected with respective external connection terminals 13A.

The larger the number of image pickup devices 11 formed on one image pickup device wafer 10W1, the higher the mass-productivity.

The connection terminals 16 are connected with the external connection terminals 13A through the via interconnects 12 (see FIG. 11) penetrating the silicon substrate. The via interconnect 12 is produced by forming a via by wet etching or dry etching and then imparting electrical conductivity to an inner surface of the via. Preferably the via interconnect is a via hole formed from the side of the rear face 15 and stopped by the rear face of the connection terminal 16 serving as an etching stop layer. The via interconnect 12 and the external connection terminal 13A are connected by the rear side interconnect 17.

Incidentally, instead of the via interconnects 12, the connection terminals 16 and the external connection terminals 13A may be connected by known lateral interconnects or the like after a dicing step or the like described later. Also, the image pickup device wafer 10W1 may be approximately circular.

<Bonding Layer Formation Step>

Figure 15:
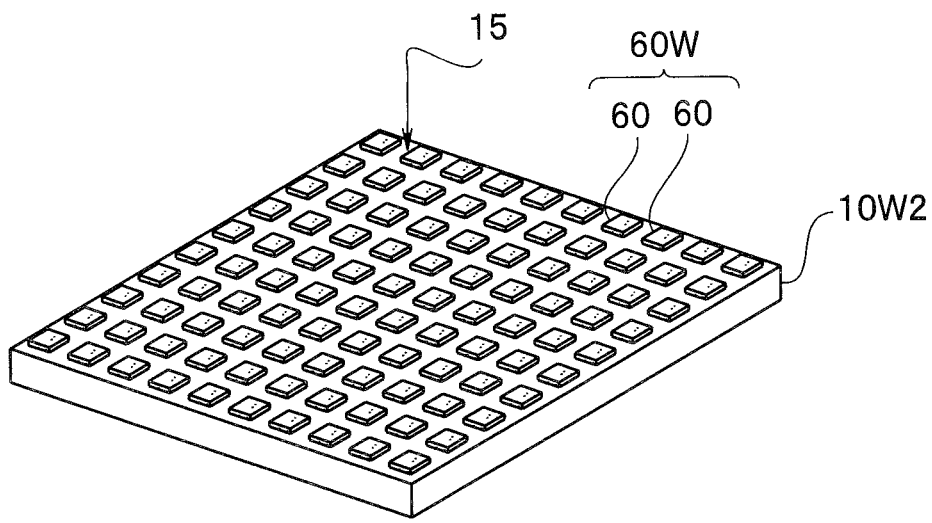
FIG. 15 is a perspective view from the side of the second main face for illustrating a bonding layer formation step of the manufacturing method for the image pickup apparatus according to the sixth embodiment.

As shown in FIG. 15, the bonding layer 60 is formed on the rear face 15 of the image pickup device wafer 10W1, being patterned to contain multiple external connection terminals 13A connected to the respective image pickup devices 11. That is, as a result of the patterning, multiple pieces of the bonding layer 60 are formed all at once on the wafer level.

Since one image pickup device 11 is connected with four external connection terminals 13A as described earlier, the bonding layer 60 is patterned to cover four external connection terminals 13A per piece. The multiple pieces of the bonding layer 60 will be referred to as a bonding layer group 60W. That is, in the bonding layer formation step, a bonding layer-lined image pickup device wafer 10W2 is produced with the bonding layer group 60W formed on the rear face 15.

For example, when the bonding layer 60 is formed using a film such as an anisotropic conductive film, after film resin is bonded to the entire rear face 15 of the image pickup device wafer 10W1, the bonding layer 60 is patterned by an etching, ashing, or other process using a metal mask.

The bonding layer 60 may be formed using nonconductive film (NCF) or using nonconductive resin paste (NCP), ACP, or liquid resin such as solder-particle-containing resin instead of film resin. When a liquid resin is used, the bonding layer 60 may be patterned using an inkjet, screen printing, or other method instead of the etching process or the like after masking.

Incidentally, if the bonding layer 60 is made of nonconductive material, regions of the external connection terminals 13A may be removed by patterning (see FIG. 23).

If the bonding layer 60 contains curing resin, preferably the resin remains uncured or partially cured during formation of the bonding layer 60. This is because the connection portions 31A and the connection terminals 16 can be connected more reliably if a curing process is performed using heating, UV irradiation, or the like in a bonding step described later.

Incidentally, each piece of the bonding layer 60 does not need to be square in external shape (projected shape) shown in FIG. 12 and the like, and may be rectangular, elliptical or the like as long as the external connection terminals 13A fit in the shape. For example, if the external shape of the image pickup device 11 is rectangular, the external shape of the bonding layer 60 may also be rectangular.

<Dicing Step>

Figure 16:
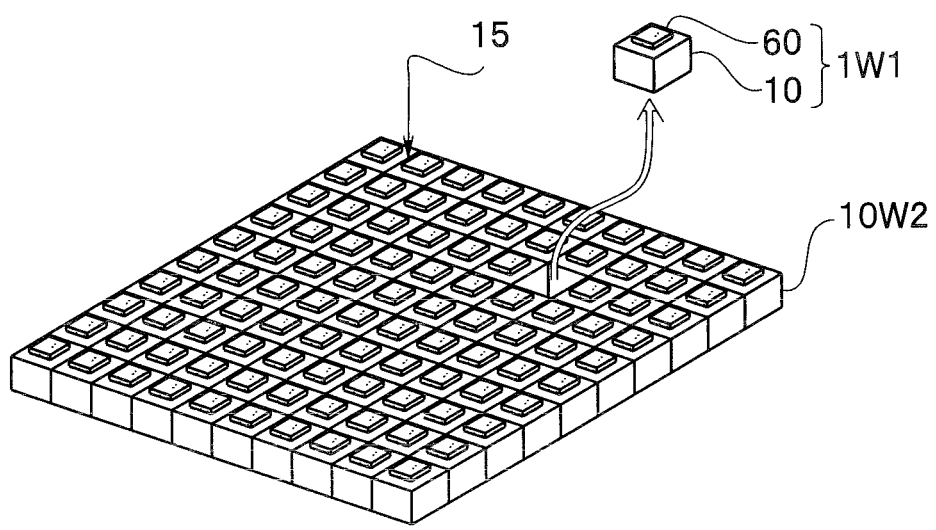
FIG. 16 is a perspective view from the side of the second main face for illustrating a dicing step of the manufacturing method for the image pickup apparatus according to the sixth embodiment.

As shown in FIG. 16, the bonding layer-lined image pickup device wafer 10W2 is cut and diced into individual image pickup device chips 1W1. Since cutting is done between pieces of the bonding layer 60, the bonding layer 60 has been formed in the center of the rear face 15 of each image pickup device chip 1W1.

A wire saw, a blade dicing saw, a laser dicing apparatus, or the like is used in a wafer cutting process of the dicing step.

<Bonding Step>

(Connection Step)

Figure 17:
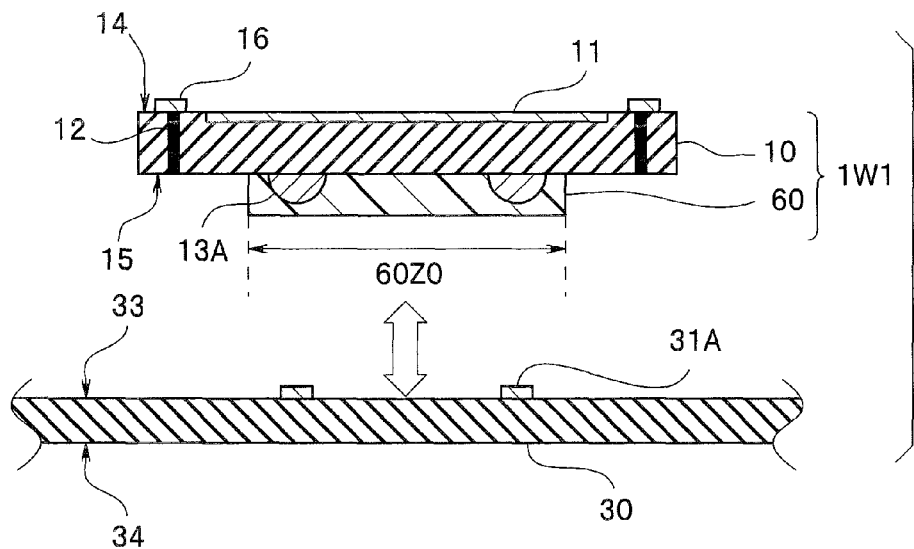
FIG. 17 is a sectional view for illustrating a bonding step of the manufacturing method for the image pickup apparatus according to the sixth embodiment.
Figure 18:
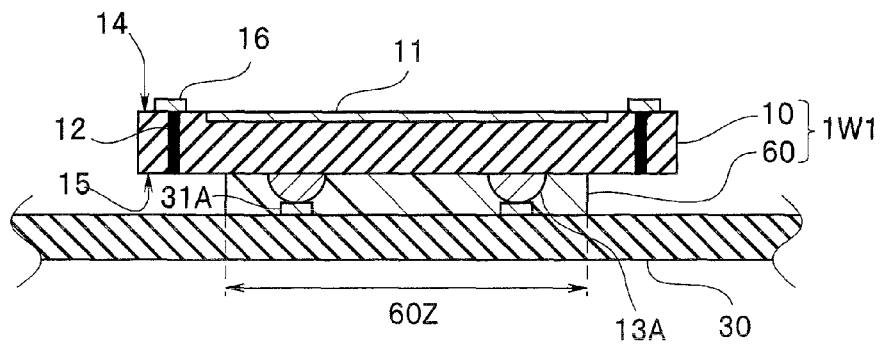
FIG. 18 is a sectional view for illustrating a connection step of the manufacturing method for the image pickup apparatus according to the sixth embodiment.

As shown in FIGS. 17 and 18, the connection portions 31A of the wiring board 30 are connected with the connection terminals 16 via the bonding layer 60. In so doing, to ensure electrical connection as well as ensure physical bonding between the image pickup device chip 10 and the wiring board 30, preferably the image pickup device chip 10 and the wiring board 30 are subjected to a bonding process by the application of pressure, i.e., attached under pressure.

The thickness of the bonding layer 60 is larger than the height of the external connection terminals 13A. Consequently, the projection plane 60Z of the bonding layer after attachment under pressure shown in FIG. 18 is larger than a projection plane 60Z0 of the bonding layer before the attachment shown in FIG. 17. That is, the bonding layer 60 has spread to lateral sides.

Incidentally, although not illustrated in FIG. 17 and the like, the electronic components 39 may be mounted on the wiring board 30 in advance as shown in FIG. 11 and the like.

(Bending Step)

Figure 19:
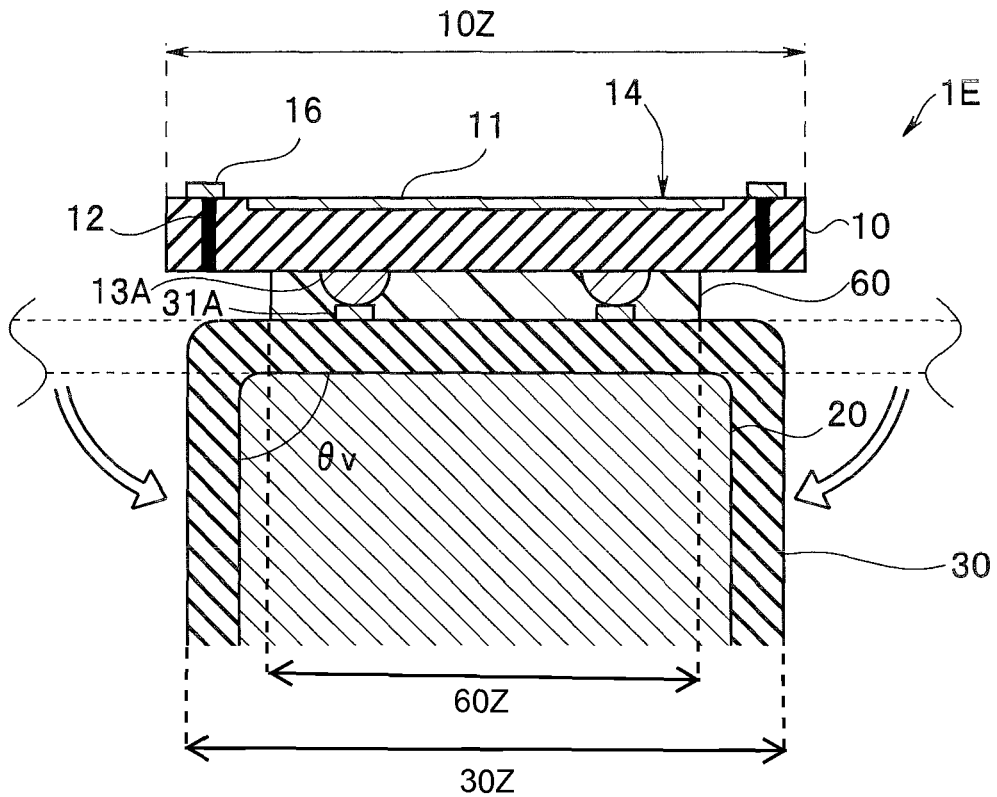
FIG. 19 is a sectional view for illustrating a bending step of the manufacturing method for the image pickup apparatus according to the sixth embodiment.

As shown in FIG. 19, the wiring board 30 is bent to place the projection plane 30Z of the wiring board within the projection plane 10Z of the image pickup device chip. Preferably the block 20 is wider than the bonding layer 60 to prevent the bonding layer 60 from being stressed during bending.

When the bending angle $\theta v$ is approximately 90 degrees or less, the wiring board 30 is placed within the projection plane 10Z of the image pickup device chip, and preferably the bending angle $\theta v$ is between 90 and 50 degrees. Incidentally, although FIG. 19 shows a U-shaped wiring board 30 bent both at the left and right sides, the wiring board may be formed into an L shape by being bent only at the other end, if provided with one short end and placed within the projection plane 10Z after bonding.

The radius of curvature of the bent portions is, for example, around 0.1 mm although this depends on the type and the like of the wiring board 30. The bonding layer 60 has been patterned into shape and size which allow for expansion of the projection plane 60Z due to attachment under pressure and the radius of curvature of the bent portions.

As described earlier, to bend the wiring board 30 at a predetermined angle and at predetermined locations as well as to reduce the stress applied to the bonding portion during bending, the block 20 is bonded to the rear face of the bonding portion 30X of the wiring board 30 in a block bonding step before the bending. Also, after the bending, the block 20 is bonded to the extension portions 30Z of the wiring board 30 placed in contact with the block 20.

Incidentally, low-profile electronic components 39 may be mounted in spaces between lateral surfaces of the bent wiring board 30 and the projection plane 10Z of the image pickup device chip.

<Cable Connection Step>

The terminal portions 32 of the extension portions 30Z connected to the wiring layer 35 of the wiring board 30 are connected with the cable 38. The cable connection is made using, for example, solder joints.

The manufacturing method according to the present embodiment enables manufacturing of the image pickup apparatus 1E which can be placed in a small space.

<Variation 1 and Variation 2 of Sixth Embodiment>

Next, variation 1 and variation 2 of the sixth embodiment will be described. The variations are similar to the sixth embodiment, and the same components as those in the sixth embodiment are denoted by the same reference numerals as the corresponding components while similar components are denoted by the same reference numerals with an alphabetical letter added to the end, and description thereof will be omitted.

Figure 20:
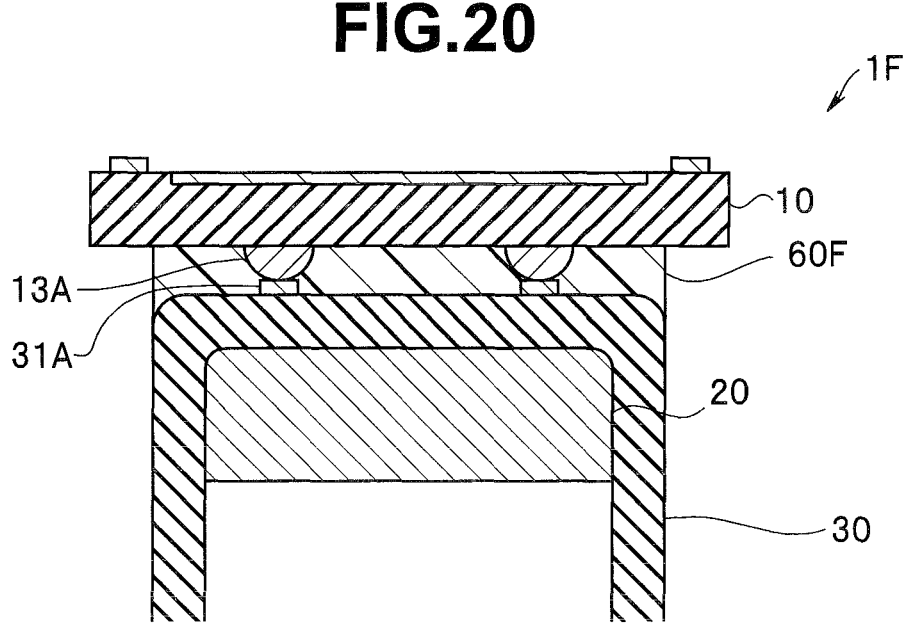
FIG. 20 is a sectional view for illustrating an image pickup apparatus according to a first variation of the sixth embodiment.

A projection plane of a bonding layer 60F of an image pickup apparatus 1F according to variation 1 of the sixth embodiment shown in FIG. 20 substantially coincides with the projection plane of the wiring board 30. On the other hand, a projection plane of a bonding layer 60G of an image pickup apparatus 1G according to variation 2 of the sixth embodiment shown in FIG. 21 is larger than the projection plane of the wiring board 30.

However, with the image pickup apparatus 1F and the image pickup apparatus 1G, the projection planes of the bonding layers 60F and 60G as well as the projection planes of the wiring boards 30 are located within the projection plane of the image pickup device chip 10.

Consequently, the image pickup apparatus 1F, the image pickup apparatus 1G, and the manufacturing method therefor according to the present variations have advantages similar to those of the image pickup apparatus 1E according to the sixth embodiment.

Incidentally, the manufacturing method for the image pickup apparatus 1G may form a bonding layer 60B by pouring a liquid resin into a gap in the bonding surface after the connection portions 31A of the wiring boards 30 and the connection terminals 16 of the image pickup device chips 10 are connected, for example, by soldering.

<Seventh Embodiment>

Next, a seventh embodiment will be described. The seventh embodiment is similar to the first embodiment and the like, and the same components as those in the first embodiment and the like are denoted by the same reference numerals as the corresponding components while similar components are denoted by the same reference numerals with an alphabetical letter added to the end, and description thereof will be omitted.

As shown in FIGS. 22A to 22C, in the image pickup apparatus 1H, 1J, and 1K according to the seventh embodiment, cut portions 17H, 17J, and 17K are formed on side faces of image pickup device chips 10H, 10J, and 10K, respectively, and the rear faces 15 are smaller in external dimensions (projection plane) than the front faces 14. A cross section of the cut portion 17H is rectangular, a cross section of the cut portion 17J is tapered, and a cross section of the cut portion 17K is sloped (curved).

Incidentally, in the seventh embodiment, the projection planes 10Z of the image pickup device chips 10H, 10J, and 10K are equal in external dimensions to the front faces 14.

In the image pickup apparatus 1H, 1J, and 1K according to the present embodiment, the projection planes 60Z of the bonding layers 60 in the bonding step are restricted in size by the cut portions 17H, 17J, and 17K. For example, the projection plane may be increased in size by capillary action if the bonding layer is formed of a liquid resin, and may be increased in size by pressure if the bonding layer is bonded under pressure. However, in the image pickup apparatus 1H, 1J, and 1K, the cut portions 17H, 17J, and 17K have a trapping function for preventing the bonding layers from expanding outward.

Consequently, the image pickup apparatus 1H, 1J, and 1K and manufacturing method according to the present embodiment have a capability to form the bonding layer 60 in a predetermined projection plane more reliably in addition to the advantages of the image pickup apparatus 1E according to the sixth embodiment and the like. Therefore, the image pickup apparatus 1H, 1J, and 1K allows the wiring boards 30 to be placed more reliably within the projection planes of the image pickup device chips 10H, 10J, and 10K.

<Eighth Embodiment>

Next, an eighth embodiment will be described. The eighth embodiment is similar to the sixth embodiment and the like, and the same components as those in the sixth embodiment and the like are denoted by the same reference numerals as the corresponding components while similar components are denoted by the same reference numerals with an alphabetical letter added to the end, and description thereof will be omitted.

As shown in FIGS. 23 and 24A, in the image pickup apparatus 1L according to the present embodiment, groove portions 18L with a rectangular cross section are formed on the rear face 15 of the image pickup device chip 10L. As shown in FIG. 23, it is sufficient if the groove portions 18L are formed at least at locations parallel to the bent portions 30Y of the wiring board 30. That is, if a wiring board bent into an L shape is used, one groove portion 18L is enough. Conversely, the groove portions may be shaped to surround the bonding layer 60.

Also, groove portions 18M of an image pickup apparatus 1M have a V-shaped cross section as shown in FIG. 24B and groove portions 18N of an image pickup apparatus 1N have a U-shaped cross section as shown in FIG. 24C. Incidentally, the groove portions 18L, 18M, and 18N may be formed to edges of the rear faces 15 of the image pickup device chips 10L, 10M, and 10N.

In the image pickup apparatus 1L, 1M, and 1N according to the present embodiment, the projection planes of the bonding layers 60L (60) in the bonding step are restricted in size by the groove portions 18L, 18M, and 18N. For example, if formed of a liquid resin, the bonding layer 60 will expand by capillary action, but the size is restricted by the groove portions 18L, 18M, and 18N.

Therefore, the image pickup apparatus 1L, 1M, and 1N and manufacturing method according to the present embodiment provides the same advantages as those of the image pickup apparatus 1H, 1J, and 1K according to the seventh embodiment and the like. Furthermore, the groove portions 18L, 18M, and 18N can be formed on the wafer level, so fabrication is easier in the present embodiment than in the image pickup apparatus 1H, 1J, and 1K according to the seventh embodiment.

Incidentally, the bonding layer 60L of the image pickup apparatus 1L shown in FIG. 23 is an example of a filmy bonding layer in which holes 60L1 are formed by removing regions around the external connection terminals 13A by patterning.

<Ninth Embodiment>

Next, a ninth embodiment will be described. The ninth embodiment is similar to the first embodiment and the like, and the same components as those in the first embodiment and the like are denoted by the same reference numerals as the corresponding components while similar components are denoted by the same reference numerals with an alphabetical letter added to the end, and description thereof will be omitted.

An image pickup apparatus 1P according to the ninth embodiment is roughly similar in structure to the image pickup apparatus 1E according to the sixth embodiment, but different from the sixth embodiment in the manufacturing method.

The manufacturing method for the image pickup apparatus 1P according to the present embodiment includes: an image pickup device chip production step of producing an image pickup device chip having an image pickup device on a first main face and an external connection terminal on a second main face, where the external connection terminal is connected to the image pickup device; a bonding layer formation step of forming a bonding layer on a wiring board having flexibility, where the bonding layer is configured to fit within a projection plane of the image pickup device chip; a bonding step of bonding together a wiring layer of the wiring board and the external connection terminal via the bonding layer; and a bending step of bending the wiring board at a bent portion so as to place the wiring board within a projection plane of the image pickup device.

Figure 25:
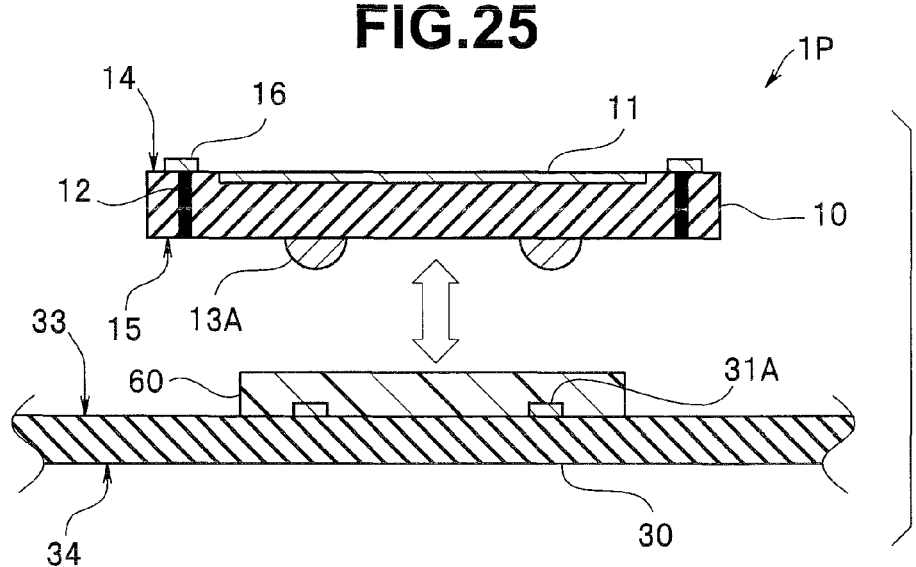
FIG. 25 is a sectional view for illustrating a manufacturing method for an image pickup apparatus according to a ninth embodiment.

That is, as shown in FIG. 25, in the image pickup device chip production step, the image pickup device chip 10 is produced by a method similar to the wafer process described earlier. On the other hand, in the bonding layer formation step, the bonding layer 60 is formed in regions containing the connection portions on the wiring board 30. The bonding layer 60 has been shaped and sized so as to fit within the projection plane of the image pickup device chip 10.

After the wiring board 30 with the bonding layer 60 formed thereon is bonded to the image pickup device chip 10 in the bonding layer formation step, the bending step is carried out.

The manufacturing method for the image pickup apparatus 1P according to the present embodiment has advantages similar to those of the manufacturing method for the image pickup apparatus 1E according to the sixth embodiment.

<Tenth Embodiment>

Next, a tenth embodiment will be described. The tenth embodiment is similar to the sixth embodiment and the like, and the same components as those in the sixth embodiment and the like are denoted by the same reference numerals as the corresponding components while similar components are denoted by the same reference numerals with an alphabetical letter added to the end, and description thereof will be omitted.

An image pickup apparatus 1Q according to the tenth embodiment is roughly similar in structure to the image pickup apparatus 1E according to the sixth embodiment, but different from the sixth embodiment in the manufacturing method.

The manufacturing method for the image pickup apparatus 1Q according to the present embodiment includes: an image pickup device chip production step of producing an image pickup device chip having an image pickup device on a first main face and an external connection terminal on a second main face, where the external connection terminal is connected to the image pickup device; a wiring board production step of producing a wiring board bent at a bent portion so as to be placed within a projection plane of the image pickup device chip; and a bonding step of bonding together a wiring layer of the wiring board and the external connection terminal via a bonding layer to be placed within the projection plane of the image pickup device chip.

Figure 26:
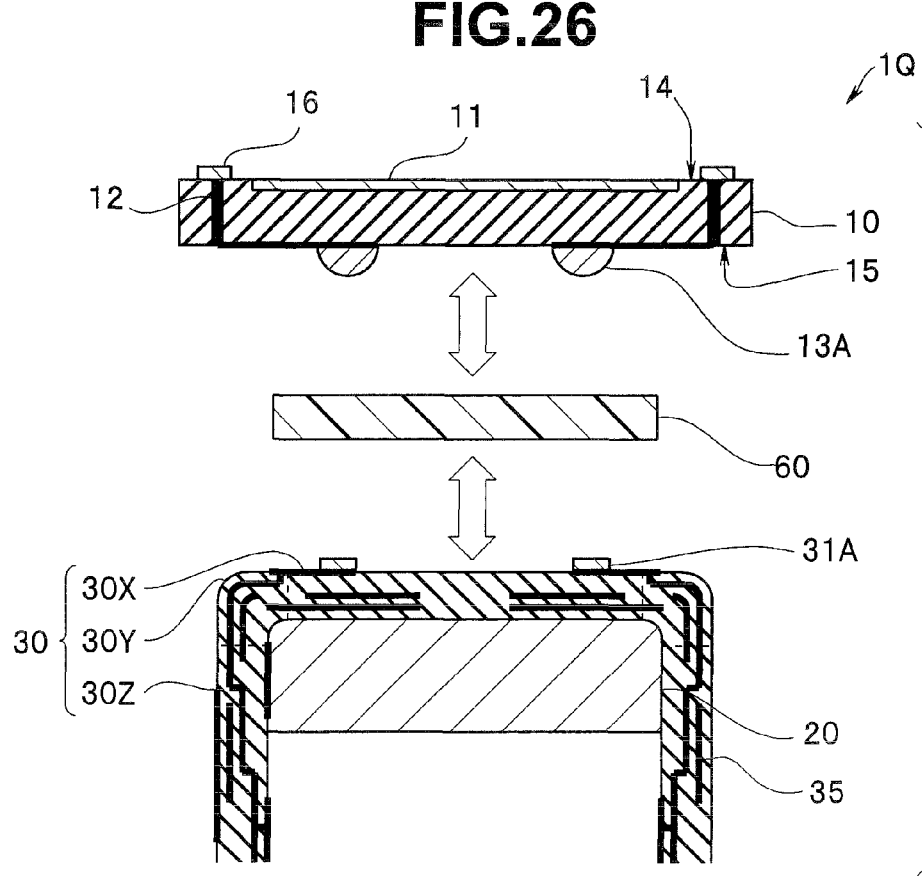
FIG. 26 is a sectional view for illustrating a manufacturing method for an image pickup apparatus according to a tenth embodiment.

That is, as shown in FIG. 26, in the manufacturing method for the image pickup apparatus 1Q, the wiring board 30 is bent at the bent portion 30Y in the wiring board production step before the bonding step. Then, in the bonding step, the bent wiring board 30 is bonded to the image pickup device chip 10 via the bonding layer 60.

Incidentally, the bonding layer 60 may be formed on either the image pickup device chip 10 or the wiring board 30. Also, the image pickup device chip 10 and the wiring board 30 may be bonded together under pressure with film resin cut to a predetermined size sandwiched therebetween.

The manufacturing method for the image pickup apparatus 1Q according to the present embodiment has advantages similar to those of the manufacturing method for the image pickup apparatus 1E according to the sixth embodiment.

<Eleventh Embodiment>

Figure 27:
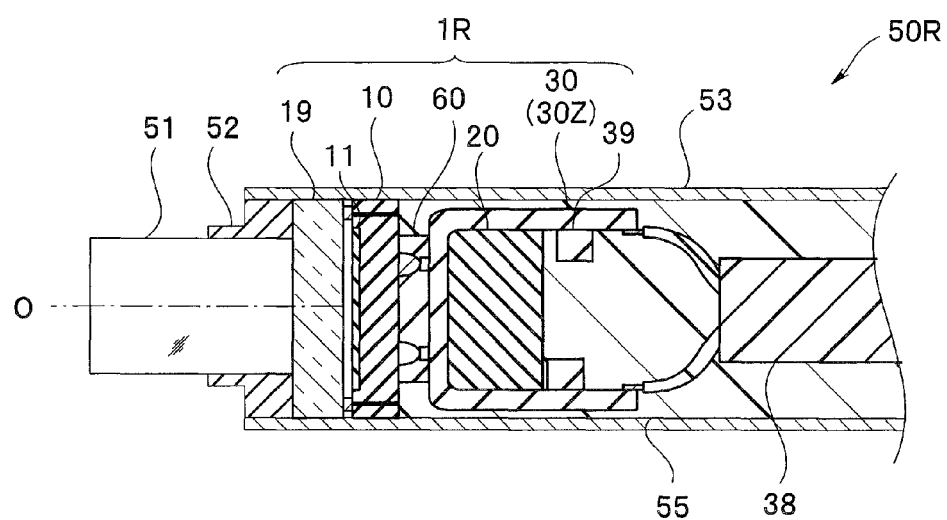
FIG. 27 is an explanatory diagram for illustrating a sectional structure of an endoscope according to an eleventh embodiment.

Next, an image pickup unit of an endoscope 50R with an image pickup apparatus 1R built into a distal end portion of an insertion portion will be described as an eleventh embodiment. The optical system 51 shown schematically in FIG. 27 and the image pickup apparatus 1R are fixed with the optical axis O as a center by the frame portion 52. A cover glass 19 which also has a function to protect the image pickup device 11 during manufacturing is bonded to a first main face of the image pickup apparatus 1R.

The image pickup apparatus 1R is housed in a small-diameter shielding frame 53, for example, with a diameter of 3 mm. The inside of the shielding frame 53 is filled with an electrically nonconductive resin filler 55 with high thermal conductivity. Electronic components 39 have been mounted on the extension portions 30Z of the wiring board 30 bent after the block 20 is disposed, and the cable 38 has been connected to a rear end portion of the wiring board 30.

The image pickup apparatus 1R has a structure similar to the image pickup apparatus 1E described earlier.

The endoscope 50R with the above structure, i.e., with the image pickup apparatus 1R and the like built into the distal end portion of the insertion portion, lends itself to diameter reduction.

<Twelfth Embodiment>

Next, description will be given of an image pickup apparatus 1S according to a twelfth embodiment, a manufacturing method for the image pickup apparatus 1S, and an endoscope 50S equipped with the image pickup apparatus 1S (hereinafter referred to as the "image pickup apparatus 1S and the like").

The image pickup apparatus 1S and the like are configured by combining appropriate features extracted from the configurations of the image pickup apparatus 1 to 1R described earlier. Specifically, the image pickup apparatus 1S includes "an image pickup device chip 10S having an image pickup device 11 on a front face 14 and an external connection terminal 13 on a rear face 15, where the external connection terminal 13 is connected to the image pickup device 11 through a via interconnect 12;" "a wiring board 30 placed within a projection plane 10Z of the image pickup device chip 10S and made up of an intermediate portion 30M whose first main face 34 is connected with the external connection terminal 13, a first flexing portion 30V1 and a second flexing portion 30V2 extended from opposite ends of the intermediate portion 30M and bent toward the intermediate portion at a predetermined angle, and a first extension portion 30C1 and a second extension portion 30C2 extended from the first flexing portion 30V1 or the second flexing portion 30V2;" "a cable 38 connected to at least one of the first extension portion 30C1 and the second extension portion 30C2;" "a block 20D to which at least part of the second main face 34 in the first extension portion 30C1 and second extension portion 30C2 of the wiring board 30 is fixed in abutment;" and "a bonding layer 60 placed in the projection plane 10Z of the image pickup device chip 10S and adapted to bond together the image pickup device chip 10S and the wiring board 30."

Furthermore, groove portions 18S are formed in the rear face 15 of the image pickup device chip 10S to restrict size of the bonding layer 60 formed of film resin or liquid resin. Also, a concave portion is formed in the block 20D to house electronic components 39 mounted on the wiring board 30.

The image pickup apparatus 1S, the manufacturing method for the image pickup apparatus 1S, and the endoscope 50S equipped with the image pickup apparatus 1S have combined advantages of the image pickup apparatus 1 and the like described earlier.

Figure 28:
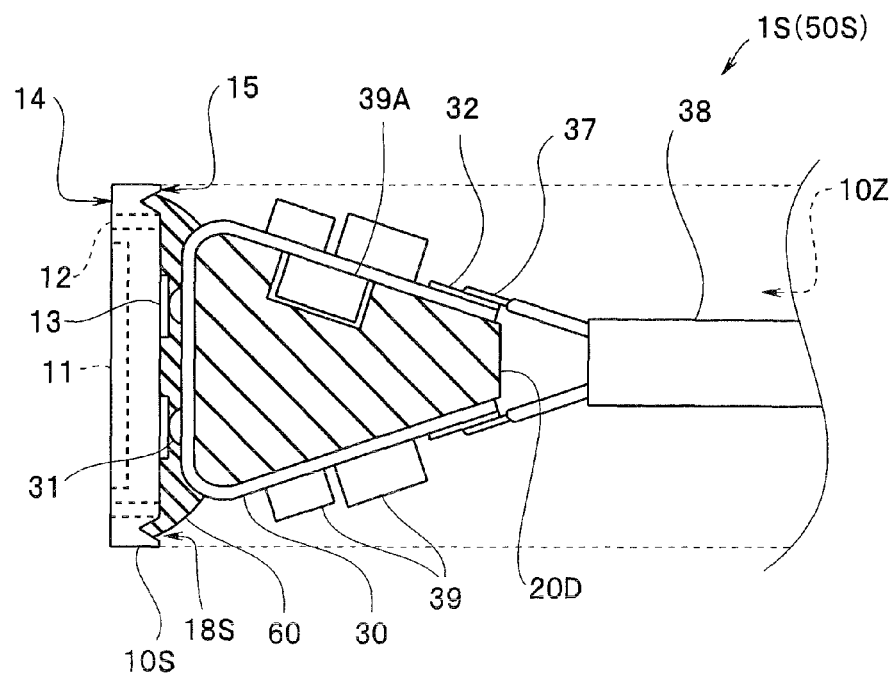
FIG. 28 is an explanatory diagram for illustrating a sectional structure of an endoscope according to a twelfth embodiment.

Also, the plate 20C shown in FIG. 9 may be used as a reinforcement member instead of the block 20D shown in FIG. 28. Also, the block 20D may be replaced with a heatsink provided with a heat dissipation function in the form of groove portions 20V formed in surfaces as in the case of the reinforcement member 20D shown in FIG. 10.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image pickup apparatus comprising:
an image pickup device chip having a front face and a rear face, the image pickup device chip comprising:
an image pickup device on the front face;
an external connection terminal on the rear face; and
a via interconnect electrically connecting the image pickup device on the front face to the external connection terminal on the rear face;
a wiring board arranged within a projection plane of the image pickup device chip, the wiring board having an exterior face and an interior face, the wiring board comprising:
an intermediate portion;
a first flexing portion having flexibility and extending from a first end of the intermediate portion;
a first extension portion extending from the first flexing portion;
a second flexing portion having flexibility and extending from a second end of the intermediate portion;
a second extension portion extending from the second flexing portion;
a connection portion arranged to the intermediate portion on the exterior face of the wiring board and being electrically connected with the external connection terminal of the image pickup device chip; and
at least one terminal portion arranged to at least one of the first extension portion and the second extension portion, wherein the at least one terminal portion is configured to be electrically connected to a signal cable; and
a reinforcement member fixed in abutment with at least a part of each of the first extension portion on the interior face of the wiring board and the second extension portion on the interior face of the wiring board.

2. The image pickup apparatus according to claim 1, further comprising a bonding layer placed in the projection plane of the image pickup device chip and adapted to bond together the image pickup device chip and the wiring board.

3. The image pickup apparatus according to claim 2, wherein the bonding layer is placed in a projection plane of the wiring board.

4. The image pickup apparatus according to claim 3, wherein a cut portion is formed on a side face of the image pickup device chip; and the rear face is smaller in external dimensions than the front face.

5. The image pickup apparatus according to claim 3, wherein a groove portion is formed in the rear face of the image pickup device chip to restrict size of the bonding layer to fit the bonding layer in the projection plane of the wiring board.

6. The image pickup apparatus according to claim 3, wherein the bonding layer is formed of film resin or liquid resin.

7. The image pickup apparatus according to claim 3, wherein an electronic component is mounted on at least one side of the wiring board.

8. The image pickup apparatus according to claim 7, wherein an opening is formed in the reinforcement member to house the electronic component mounted on the interior face of the wiring board.

9. The image pickup apparatus according to claim 3, wherein the reinforcement member has a groove portion in a surface.

10. The image pickup apparatus according to claim 1, wherein:
the first flexing portion is bent such that a first angle between the intermediate portion and the first extension portion extending from the first flexing portion is less than 90 degrees, and
the second flexing portion is bent such that a second angle between the intermediate portion and the second extension portion extending from the second flexing portion is less than 90 degrees, and
wherein the wiring board is arranged within the projection plane of the image pickup device chip by the bending of the first flexing portion and the second flexing portion.

11. An endoscope comprising:
an image pickup device chip having a front face and a rear face, the image pickup device chip comprising:
an image pickup device on the front face;
an external connection terminal on the rear face; and
a via interconnect electrically connecting the image pickup device on the front face to the external connection terminal on the rear face;
a wiring board arranged within a projection plane of the image pickup device chip, the wiring board having an exterior face and an interior face, the wiring board comprising:
an intermediate portion;
a first flexing portion having flexibility and extending from a first end of the intermediate portion;
a first extension portion extending from the first flexing portion;
a second flexing portion having flexibility and extending from a second end of the intermediate portion;
a second extension portion extending from the second flexing portion;
a connection portion arranged to the intermediate portion on the exterior face of the wiring board and being electrically connected with the external connection terminal of the image pickup device chip; and
at least one terminal portion arranged to at least one of the first extension portion and the second extension portion, wherein the at least one terminal portion is configured to be electrically connected to a signal cable; and a reinforcement member fixed in abutment with at least a part of each of the first extension portion on the interior face of the wiring board and the second extension portion on the interior face of the wiring board.

12. The endoscope according to claim 11, further comprising a bonding layer placed in the projection plane of the image pickup device chip and adapted to bond together the image pickup device chip and the wiring board.

13. A method for manufacturing an image pickup apparatus, the method comprising:
an external connection terminal connection step of connecting an image pickup device chip to a wiring board, wherein the image pickup device chip has a front face and a rear face, and the image pickup device chip comprises:
an image pickup device on the front face;
an external connection terminal on the rear face; and
a via interconnect electrically connecting the image pickup device on the front face to the external connection terminal on the rear face;
wherein the wiring board has an exterior face and an interior face, and the wiring board comprises:
an intermediate portion;
a first flexing portion having flexibility and extending from a first end of the intermediate portion;
a first extension portion extending from the first flexing portion;
a second flexing portion having flexibility and extending from a second end of the intermediate portion;
a second extension portion extending from the second flexing portion;
a connection portion arranged to the intermediate portion on the exterior face of the wiring board; and
at least one terminal portion arranged to at least one of the first extension portion and the second extension portion,
wherein the external connection terminal connection step comprises electrically connecting the external connection terminal of the image pickup device chip to the connection portion of the wiring board;
a reinforcement member bonding step of bonding a reinforcement member to the intermediate portion on the interior face of the wiring board;
a wiring board fixing step of:
bending the first flexing portion toward the intermediate portion at a predetermined angle,
fixing the reinforcement member in abutment with at least a part of the first extension portion on the interior face of the wiring board,
bending the second flexing portion toward the intermediate portion at the predetermine angle, and
fixing the reinforcement member in abutment with at least a part of the second extension portion on the interior face of the wiring board,
thereby placing the wiring board within a projection plane of the image pickup device chip; and
a cable connection step of electrically connecting a signal cable to the at least one terminal portion of the wiring board.

14. The manufacturing method for an image pickup apparatus, according to claim 13, further comprising an image pickup device chip production step of producing the image pickup device chip, the image pickup device chip production step comprising:
an image pickup device wafer production step of producing an image pickup device wafer comprising a plurality of the image pickup device on a front face of the image pickup device wafer and a plurality of the external connection terminal on a rear face of the image pickup device wafer, where each of the plurality of the external connection terminal is connected to a corresponding one of the plurality of the image pickup device;
a bonding layer formation step of forming a plurality of bonding layers on the rear face of the image pickup device wafer, with each bonding layer being patterned to contain a group of the external connection terminal in the plurality of the external connection terminal; and
a dicing step of dicing the image pickup device wafer into a plurality of the image pickup device chip, the image pickup device chip being larger in external dimensions than the bonding layer; and
wherein in the external connection terminal connection step, the image pickup device chip is connected to the wiring board by connecting the bonding layer of the image pickup device chip to the wiring board.

15. The manufacturing method for an image pickup apparatus, according to claim 14, wherein:
the image pickup device chip production step further comprises a cut portion formation step of forming a cut portion on a side face of the image pickup device chip; and
the rear face of the image pickup device chip is smaller in external dimensions than the front face of the image pickup device chip.

16. The manufacturing method for an image pickup apparatus, according to claim 14, wherein the image pickup device chip production step further comprises a groove portion forming step of forming a groove portion in the rear face of the image pickup device chip to restrict the size of the bonding layer to fit the bonding layer in a projection plane of the wiring board.

* * * * *